US009795720B2

(12) United States Patent
Chappa et al.

(10) Patent No.: US 9,795,720 B2
(45) Date of Patent: *Oct. 24, 2017

(54) COATINGS WITH CRYSTALLIZED ACTIVE AGENT(S) AND METHODS

(71) Applicant: Surmodics, Inc., Eden Prairie, MN (US)

(72) Inventors: Ralph A. Chappa, Ham Lake, MN (US); Kimberly K. M. Lindsoe, Eden Prairie, MN (US)

(73) Assignee: Surmodics, Inc., Eden Prairie, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/211,833

(22) Filed: Jul. 15, 2016

(65) Prior Publication Data

US 2017/0007745 A1 Jan. 12, 2017

Related U.S. Application Data

(63) Continuation of application No. 14/753,186, filed on Jun. 29, 2015, now Pat. No. 9,649,413, which is a continuation of application No. 12/636,164, filed on Dec. 11, 2009, now Pat. No. 9,427,501, which is a continuation of application No. 11/295,167, filed on Dec. 6, 2005, now abandoned.

(60) Provisional application No. 60/634,070, filed on Dec. 7, 2004.

(51) Int. Cl.
| A61K 47/32 | (2006.01) |
| A61K 31/56 | (2006.01) |
| A61L 31/16 | (2006.01) |
| A61K 6/00 | (2006.01) |
| A61L 27/34 | (2006.01) |
| A61L 27/50 | (2006.01) |
| A61L 27/54 | (2006.01) |
| A61L 31/10 | (2006.01) |
| A61L 31/14 | (2006.01) |

(52) U.S. Cl.
CPC ............ *A61L 31/16* (2013.01); *A61K 6/0017* (2013.01); *A61K 31/56* (2013.01); *A61L 27/34* (2013.01); *A61L 27/50* (2013.01); *A61L 27/54* (2013.01); *A61L 31/10* (2013.01); *A61L 31/14* (2013.01); *A61L 2300/216* (2013.01); *A61L 2300/222* (2013.01); *A61L 2300/43* (2013.01); *A61L 2300/602* (2013.01); *A61L 2300/606* (2013.01); *A61L 2300/63* (2013.01); *A61L 2420/02* (2013.01); *A61L 2420/06* (2013.01)

(58) Field of Classification Search
None
See application file for complete search history.

(56) References Cited

U.S. PATENT DOCUMENTS

| 4,638,045 | A | 1/1987 | Kohn et al. |
| 5,466,233 | A | 11/1995 | Weiner et al. |
| 5,676,764 | A | 10/1997 | Locklin et al. |
| 5,797,887 | A | 8/1998 | Rosen et al. |
| 6,214,901 | B1 | 4/2001 | Chudzik et al. |
| 6,235,306 | B1 | 5/2001 | Miranda et al. |
| 6,273,913 | B1 | 8/2001 | Wright et al. |
| 6,344,035 | B1 | 2/2002 | Chudzik et al. |
| 6,369,039 | B1 | 4/2002 | Palasis et al. |
| 6,719,750 | B2 | 4/2004 | Varner et al. |
| 6,890,583 | B2 | 5/2005 | Chudzik et al. |
| 7,008,667 | B2 | 3/2006 | Chudzik et al. |
| 7,097,850 | B2 | 8/2006 | Chappa et al. |
| 7,976,862 | B2 | 7/2011 | Anderson et al. |
| 9,427,501 | B2 | 8/2016 | Chappa et al. |
| 9,649,413 | B2 | 5/2017 | Chappa et al. |
| 2002/0091433 | A1 | 7/2002 | Ding et al. |
| 2003/0014036 | A1 | 1/2003 | Varner et al. |
| 2003/0144727 | A1 | 7/2003 | Rosenthal et al. |
| 2003/0232122 | A1 | 12/2003 | Chappa et al. |
| 2004/0062852 | A1 | 4/2004 | Schroeder et al. |
| 2004/0062875 | A1 | 4/2004 | Chappa et al. |
| 2004/0086569 | A1 | 5/2004 | Hobot et al. |
| 2004/0133155 | A1 | 7/2004 | Varner et al. |
| 2005/0019371 | A1 | 1/2005 | Anderson et al. |
| 2005/0059956 | A1 | 3/2005 | Varner et al. |
| 2005/0143363 | A1 | 6/2005 | De Juan et al. |
| 2005/0271703 | A1 | 12/2005 | Anderson et al. |
| 2005/0271706 | A1 | 12/2005 | Anderson et al. |
| 2005/0276837 | A1 | 12/2005 | Anderson et al. |
| 2005/0281863 | A1 | 12/2005 | Anderson et al. |

(Continued)

FOREIGN PATENT DOCUMENTS

| EP | 1819373 | 8/2007 |
| WO | 2002055122 | 7/2002 |

(Continued)

OTHER PUBLICATIONS

"Amorphous Solids: Implications for Solubility and Stability," SSCI Application Note, (2006) 3 pages.

(Continued)

*Primary Examiner* — Abigail Vanhorn

(74) *Attorney, Agent, or Firm* — Pauly, DeVries Smith & Deffner LLC

(57) ABSTRACT

Aspects herein relate to coatings with crystallized active agent(s) and related methods. A method for coating a medical device herein includes selecting a solvent and a polymer, selecting a concentration of an active agent of at least a certain amount of saturation, forming a coating composition having the selected concentration of the active agent, and applying the coating composition to the medical device.

6 Claims, 5 Drawing Sheets

(56) References Cited

U.S. PATENT DOCUMENTS

| | | |
|---|---|---|
| 2005/0287188 A1 | 12/2005 | Anderson et al. |
| 2006/0110428 A1 | 5/2006 | De Juan et al. |
| 2006/0134168 A1 | 6/2006 | Chappa et al. |
| 2007/0248637 A1 | 10/2007 | Chappa et al. |
| 2010/0093686 A1 | 4/2010 | Chappa |
| 2011/0268786 A1 | 11/2011 | Jasch et al. |
| 2014/0066304 A1 | 3/2014 | Alexander et al. |
| 2015/0374886 A1 | 12/2015 | Chappa et al. |

FOREIGN PATENT DOCUMENTS

| | | |
|---|---|---|
| WO | 03045448 | 6/2003 |
| WO | 2006063021 | 6/2006 |

OTHER PUBLICATIONS

Brandup, et al., "Polymer Handbook," 4th ed. John Wiley & Sons, N.Y. (1999) pp. 675-710.

"Chlorinated Solvents," Product information for Dow Chemical Company, http://www.meridianeng.com/chlorina.html. (2008), 7 pages.

"Communication pursuant to Article 94(3) EPC," for EP Patent Application No. 05853187.2, mailed Feb. 28, 2011, (5 pages).

"Communication Pursuant to Article 94(3) EPC," for European Patent Application No. 05853187.2, mailed Apr. 29, 2009 (5 pages).

"Communication Pursuant to Article 94(3) EPC," for European Patent Application No. 05853187.2, mailed Dec. 18, 2007 (5 pages).

File History for U.S. Appl. No. 12/636,164, downloaded Oct. 5, 2016 (292 pages).

"Handbook of Chemistry and Physics," 57th Edition (1997), 3 pages.

"International Preliminary Report on Patentability," for PCT/US2005/044198, mailed Jun. 21, 2007 (8 pages).

"International Search Report and Written Opinion," for PCT/US2005/044198, mailed Aug. 23, 2006 (6 pages).

Kotiyan, Pramila N. et al., "Eudragits: Roles as Crystallization Inhibitors in Drug-In-Adhesive Transdermal Systems of Estradiol," European Journal of Pharmaceutics and Biopharmaceutics vol. 52, Issue 2 Sep. 2001, 173-180.

Ma, Xinghang et al., "Control of drug crystallization in transdermal matrix system," International Journal of Pharmaceutics, vol. 142, Issue 1 (1996), pp. 115-119.

"Non-Final Office Action," for U.S. Appl. No. 11/295,167, mailed Apr. 28, 2009 (61 pages).

"Non-Final Office Action," for U.S. Appl. No. 14/753,186 mailed Aug. 22, 2016 (21 pages).

"Response to Communication Pursuant to Article 94(3) EPC," for European Patent Application No. 05853187.2, mailed Apr. 29, 2009 and filed with the EPO Oct. 28, 2009 (5 pages).

"Response to Communication Pursuant to Article 94(3) EPC," for European Patent Application No. 05853187.2, mailed Dec. 18, 2007 and filed with the EPO Apr. 1, 2008 (33 pages).

"Response to Communication Pursuant to Article 94(3) EPC," for European Patent Application No. 05853187.2, mailed Feb. 28, 2011 and filed with the EPO Jun. 14, 2011 (8 pages).

"Response to Non-Final Office Action," for U.S. Appl. No. 11/295,167, mailed Apr. 28, 2009 and filed with the USPTO Aug. 28, 2009 (16 pages).

Shekunov, B. Y. et al., "Crystallization process in pharmaceutical technology and drug delivery design," Journal of Crystal Growth; 211, (2000), pp. 122-136.

"Sigma-Aldrich Solvent Lists for Toluene and THF," htto://www.sigmaaldrich.com/catalog/search/ProductDetail/SIAL/179418 and http:www.sigmaaldrich.com/catalog/search/ProductDetail/ SIAL/360589 (2008) 6 pages.

Stromberg, Thomas et al., "Rapamycin sensitizes multiple myeloma cells to apoptosis induced by dexamethasone," Blood, Apr. 15, 2004, vol. 103, No. 8, retrieved Aug. 15, 2016 (11 pages).

"Response to Non-Final Office Action," for U.S. Appl. No. 14/753,186, mailed Aug. 22, 2016 and filed with the USPTO Nov. 22, 2016 (13 pages).

A

D

B

E

C

F

A

B

COATINGS WITH CRYSTALLIZED ACTIVE AGENT(S) AND METHODS

This application is a continuation of U.S. application Ser. No. 14/753,186, filed Jun. 29, 2015 which is a continuation of U.S. application Ser. No. 12/636,164, filed Dec. 11, 2009, which is a continuation of U.S. application Ser. No. 11/295,167, filed Dec. 6, 2005 which claims the benefit of U.S. Provisional Application No. 60/634,070, filed Dec. 7, 2004, the contents of which are herein incorporated by reference.

FIELD OF THE INVENTION

The present invention relates to coating compositions and related methods. More specifically, the present invention relates to coatings with crystallized active agent(s) and related methods.

BACKGROUND OF THE INVENTION

Therapeutic benefits can be achieved in some instances by providing an active agent to a specific target tissue, instead of systemically. This is because the effect of the agent on the target tissue can be maximized while limiting side effects on other tissues. Therapeutic benefits can also be achieved by providing an active agent to a subject in a manner that extends the time over which the active agent is released. One approach to providing these benefits is to use a coating system containing an active agent on a medical device.

Predictability and consistency of the elution rate of an active agent from a coating or material on devices is of importance, particularly in the clinical context. Specifically, in some applications it can be problematic if two devices manufactured in the same batch have significantly different elution rates, or if the elution rates vary significantly between separate batches. Finally, shelf stability of coated devices is of significance as an excessively short shelf-life may raise costs associated with maintaining an inventory sufficient to meet demand.

Accordingly, there is a need for coatings and methods of coating providing consistent elution rates. There is also a need for coatings and methods of coating providing adequate shelf-stability.

SUMMARY OF THE INVENTION

The present invention relates to coatings with crystallized active agent(s) and related methods. In an embodiment, the invention includes a method for coating a medical device including selecting a solvent and a polymer, selecting a concentration of an active agent of at least a certain amount of saturation, forming a coating composition having the selected concentration of the active agent, and applying the coating composition to the medical device. In an embodiment, the invention includes an elution control coating disposed on a medical device, the elution control coating including a polymer, and an active agent, wherein the active agent is at least about 80% crystallized within one week of being disposed on the medical device. In an embodiment, the invention includes a method for enhancing the formation of active agent crystals within a coating layer including forming a coating solution and adjusting the concentration of the active agent in the coating solution to reach some percentage of the active agent saturation point. In an embodiment, the invention includes a method of enhancing crystallization of an active agent, the method including forming a coating solution comprising a polymer, an active agent, and a solvent; applying the coating solution to a substrate; and increasing the rate of active agent nucleation within the coating.

Figure 1:
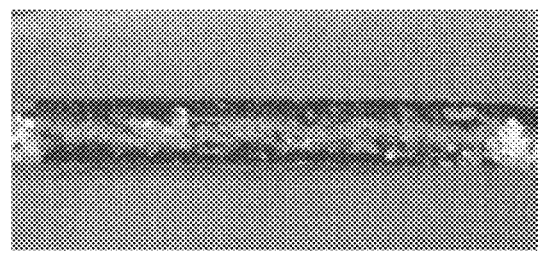
FIG. 1 is a microscopic view of a coating on a device taken under polarizing light.

While the invention is susceptible to various modifications and alternative forms, specifics thereof have been shown by way of example and drawings, and will be described in detail. It should be understood, however, that the invention is not limited to the particular embodiments described. On the contrary, the intention is to cover modifications, equivalents, and alternatives falling within the spirit and scope of the invention.

DETAILED DESCRIPTION OF THE INVENTION

As used herein, the term "solubility" refers to the amount of a substance (called the solute) that can be dissolved in given quantity of another substance (called the solvent) at given environmental conditions, such as at a given temperature.

As used herein, the term "saturated" shall refer to the condition wherein a solvent cannot dissolve any more of a solute (such as an "active agent") at a given temperature and pressure. As used herein, the term saturated shall also include the condition of supersaturation.

As used herein, the term "supersaturated" shall refer to the condition where more of a solute is dissolved in a solvent than is stable at a given temperature. Supersaturation may occur in instances such as when a saturated solution is cooled down.

In some coating systems used for drug delivery, the coating is applied to a substrate as a coating solution containing polymer(s), active agent(s), and solvent(s). Typically, the solvents evaporate from the coating solution during and/or after application to the substrate to form a coating layer or layers. In some cases, the active agent crystallizes over a period of days, weeks, or even months. The final extent of crystallization (e.g., the percentage of the total active agent that eventually turns into a crystalline form) depends on many factors including the particular active agent being used, the polymers used, the amount of residual solvent, the presence of other components such as additives or impurities, etc. In some cases, substantially all of the active agent crystallizes. In other cases, virtually none of the active agent crystallizes. In still other cases, some percentage of the active agent crystallizes while the rest remains non-crystalline (or amorphous).

Batch-to-batch consistency of active agent elution rates for coated devices can be affected by the extent of crystallization. For some active agents, elution of a crystalline form is slower than elution of a non-crystalline form. This is because solvation of the compound generally occurs before the compound can be eluted and crystalline forms generally form solvates more slowly than otherwise similar non-crystalline forms. Thus, for the sake of elution consistency, it is desirable to have some degree of consistency regarding the total percentage of the active agent that crystallizes from batch to batch. Embodiments of the invention can increase elution consistency by enhancing the crystallization process resulting in more rapid and uniform crystallization within and across batches.

In addition, where the crystallization process occurs relatively slowly, such as over multiple days or weeks, the percentage of active agent crystallizing is more likely to be affected by other variables such as post-manufacturing temperature and humidity, and this can affect both batch-to-batch elution consistency as well as intra-batch elution consistency. For example, a device that is subject to relatively colder transport and/or storage conditions between the time of manufacturing and end use may exhibit a greater degree of crystallization in contrast to a device manufactured as a part of the same batch but that was subject to warmer transport and/or storage conditions. Embodiments of the invention can increase elution consistency by speeding up the crystallization process resulting in devices that are less susceptible to variations in transport and/or storage conditions.

In addition, active agents are more stable in a crystalline form. Thus, enhancing the crystallization process can enhance the stability of active agents in coatings. Embodiments of the invention can include coatings with active agents having enhanced stability because they are in a crystalline form.

Sometimes, during the crystallization process that occurs after a coating solution is applied to a substrate, crystals form in a manner such that they break-through, or erupt from, the surface of the coating. If enough crystals erupt through the surface of the coating, the performance of the coating may be compromised. For example, active agent that is not covered by any coating material will elute off faster than active agent that is disposed within the coating material. Thus, crystals erupting through the surface can cause the initial elution burst to be increased, potentially to an undesirable level. It is believed that the process of crystals erupting from the surface of a coating is related to average crystal size. Specifically, it is believed that larger crystals erupt from the surface of a coating to a greater extent than do smaller crystals. In many cases, a more rapid crystallization process results in a smaller crystal size on average than does a slower crystallization process. Embodiments of the invention can increase the speed of the crystallization process resulting in the formation of smaller crystals that are less likely to erupt from the surface of a coating than are larger crystals.

Crystallization involves the formation of a solid aggregate in which the plane faces intersect at definite angles and in which there is a regular internal structure of the constituent chemical species. Nucleation is the formation in a solution of a number of minute solid bodies, embryos, nuclei or seeds that then act as centers of crystallization. Nucleation may occur spontaneously or it may be induced artificially. Nucleation can be classified as either primary or secondary. Primary nucleation refers to all cases of nucleation in systems that do not contain crystalline matter to start. Primary nucleation can be further divided into homogeneous primary nucleation, which is spontaneous primary nucleation, and heterogeneous primary nucleation which is primary nucleation induced by foreign particles. Secondary nucleation refers to nucleation induced by crystals. Crystallization depends on both the condition of supersaturation (as defined above) and the process of nucleation. Accordingly, crystallization can be enhanced or accelerated by increasing the degree of supersaturation and/or enhancing the nucleation process.

In some embodiments of the invention, crystallization is enhanced by increasing the degree of supersaturation or increasing the speed with which the coating solution becomes supersaturated during or after application to a substrate. By way of example, it has been discovered that adjusting the concentration of an active agent in a coating solution to a point, by way of example to the saturation point, enhances rapid crystal formation. For example, assuming a solution containing active agent is at the limit of solubility, as soon as some solvent starts to evaporate, the remaining solvent becomes supersaturated with the active agent. This rapid state of supersaturation causes crystallization to occur more rapidly and frequently more consistently. In an embodiment, the invention includes a method for coating a medical device including selecting a solvent and a polymer, selecting a concentration of an active agent of at least 80% of saturation in a composition comprising the solvent and about 1.0 to about 99.0 wt. % polymer, combining the active agent, the polymer, and the solvent to form a coating composition having the selected concentration of the active agent, and applying the coating composition to the medical device. In an embodiment, the invention includes a method for rapidly crystallizing an active agent in a coating layer including combining a polymer, an active agent, and a solvent to form a coating solution having between 5 mg/ml and 200 mg/ml total solids concentration, adjusting the concentration of the active agent in the coating solution to reach at least 80% of the active agent saturation point, applying the coating solution to a device, and evaporating the solvent to form crystals of the active agent.

Embodiments of the invention can include coatings that can be used to control the elution rate of active agents therefrom. In an embodiment, the invention includes an elution control coating disposed on a medical device, the elution control coating including a polymer, and an active agent, wherein the active agent is at least about 80% crystallized within one week of being disposed on the medical device. In an embodiment, the active agent is at least about 90% crystallized within one week of being disposed on the medical device. The active agent can be at least about 95% crystallized within one week of being disposed on the medical device. The active agent can be at least about 95% crystallized within one day of being disposed on the medical device.

In some embodiments, supersaturation is increased by addition of a component to a coating solution that decreases solubility of the active agent in the solvent.

In some embodiments of the invention, crystallization is enhanced by enhancing the nucleation process. By way of example, in some embodiments, nucleation is enhanced by seeding the coating solution as it is applied with crystals of the active agent. In other embodiments, nucleation is enhanced by the addition of foreign particles to the coating solution that function to trigger heterogeneous primary nucleation.

Coating Composition:

Coating compositions used in embodiments of the invention can include components such as polymer(s), solvent(s), active agent(s), additives, etc. In an embodiment, the coating composition is saturated with active agent or near saturation. In an embodiment, the concentration of active agent in the coating composition is at least 60% of saturation limit at an ambient temperature. In an embodiment, the concentration of active agent in the coating composition is at least 70% of the saturation limit at an ambient temperature. In an embodiment, the concentration of active agent in the coating composition is at least 80% of the saturation limit at an ambient temperature. In an embodiment, the concentration of active agent in the coating composition is at least 90% of the saturation limit at an ambient temperature. In an embodiment, the concentration of active agent in the coating composition is at least 95% of the saturation limit at an ambient temperature. In an embodiment, the concentration of active agent in the coating composition is at least 99% of the saturation limit at an ambient temperature. In an embodiment, the concentration of active agent in the coating composition is at least 100% of the saturation limit at an ambient temperature.

In some embodiments, the coating solution can be characterized with respect to the total amount of solids in the composition including the active agent and polymer(s). In an embodiment, the total amount of solids concentration in the solution is between 5 mg/ml and 200 mg/ml. In an embodiment, the total solids concentration is between 10 mg/ml and 80 mg/ml. In an embodiment, the total solids concentration is between 20 mg/ml and 60 mg/ml. In an embodiment, the total solids concentration is between 30 mg/ml and 50 mg/ml. In an embodiment, the total solids concentration is about 40 mg/ml.

In some embodiments, the coating solution includes a first solvent and a second solvent, wherein the active agent is insoluble or only sparingly soluble in the first solvent but soluble or freely soluble in the second solvent. In an embodiment, the polymer(s) of the coating composition are soluble in both the first and second solvent. One method of preparing the coating composition with two solvents, wherein the active agent is only soluble in one of them, includes mixing the polymer(s) with the particular solvent that the active agent is insoluble or only sparingly soluble in, then mixing the active agent with the other solvent, and finally combining the two solutions in various proportions until it is determined what percentage of the first solvent causes the active agent to start precipitating out of the solution. A coating solution can then be prepared with a percentage of the first solvent that pushes the amount of active agent to the saturation limit for the relative proportions of the two solvents being used.

The coating composition may also include other components. By way of example, the coating composition may include agents that aid in the nucleation process (homogenous or heterogenous) to enhance crystallization. In an embodiment, the composition may include a component that serves as a seed. This component may include crystallized active agent or another compound that enhances the crystallization process. In an embodiment, a component that triggers heterogeneous nucleation is deposited onto a substrate and then the coating solution is deposited onto that component.

The coating composition may also include other components that enhance crystallization. By way of example, the coating composition may include other solvents that enhance crystallization of a particular active agent.

Solvents:

Many different solvents can be used with embodiments of the present invention depending on the particular polymers and active agents used. Solvents can include water, alcohols (e.g., methanol, butanol, propanol, and isopropanol (isopropyl alcohol)), alkanes (e.g., halogenated or unhalogenated alkanes such as hexane and cyclohexane), amides (e.g., dimethylformamide), ethers (e.g., THF and dioxolane), ketones (e.g., methylethylketone), aromatic compounds (e.g., toluene and xylene), nitriles (e.g., acetonitrile) and esters (e.g., ethyl acetate). In an embodiment, the solvent is one in which a polymer component(s) forms a true solution.

In an embodiment, the invention includes a first solvent and a second solvent, wherein the active agent is soluble or freely soluble in the first solvent but insoluble or only sparingly soluble in the second solvent. In an embodiment, the first solvent can be THF. In an embodiment, the second solvent can be toluene. In an embodiment, the first solvent has a higher vapor pressure than the second solvent and is thus more volatile than the second solvent.

Polymers

Coating solutions used in embodiments of the invention can include one or more polymers. In an embodiment, the coating solution includes a plurality of polymers, including a first polymer and a second polymer. When the coating solution contains only one polymer, it can be either a first or second polymer as described herein. As used herein, term "(meth)acrylate" when used in describing polymers shall mean the form including the methyl group (methacrylate) or the form without the methyl group (acrylate).

Examples of suitable first polymers include poly(alkyl (meth)acrylates), and in particular, those with alkyl chain lengths from 2 to 8 carbons, and with molecular weights from 50 kilodaltons to 900 kilodaltons. An exemplary first polymer is poly(n-butyl methacrylate) (pBMA). Such polymers are available commercially, e.g., from Aldrich, with molecular weights ranging from about 200,000 Daltons to about 320,000 Daltons, and with varying inherent viscosity, solubility, and form (e.g., as crystals or powder).

Examples of suitable first polymers also include polymers selected from the group consisting of poly(aryl(meth)acrylates), poly(aralkyl (meth)acrylates), and poly(aryloxyalkyl (meth)acrylates). Such terms are used to describe polymeric structures wherein at least one carbon chain and at least one aromatic ring are combined with acrylic groups, typically esters, to provide a composition. In particular, exemplary polymeric structures include those with aryl groups having from 6 to 16 carbon atoms and with weight average molecular weights from about 50 to about 900 kilodaltons. Suitable poly(aralkyl(meth)acrylates), poly(arylalky(meth)acrylates) or poly(aryloxyalkyl (meth)acrylates) can be made from aromatic esters derived from alcohols also containing aromatic moieties. Examples of poly(aryl(meth)acrylates) include poly(9-anthracenyl methacrylate), poly(chlorophenylacrylate), poly(methacryloxy-2-hydroxybenzophenone), poly(methacryloxybenzotriazole), poly(naphthylacrylate) and -methacrylate), poly(4-nitrophenyl acrylate), poly(pentachloro(bromo, fluoro) acrylate) and -methacrylate), and poly(phenyl acrylate) and -methacrylate). Examples of poly(aralkyl (meth)acrylates) include poly(benzyl acrylate) and -methacrylate), poly(2-phenethyl acrylate) and -methacrylate, and poly(1-pyrenylmethyl methacrylate). Examples of poly(aryloxyalkyl (meth)acrylates) include poly(phenoxyethyl acrylate) and -methacrylate), and poly(polyethylene glycol phenyl ether acrylates) and -methacrylates with varying polyethylene glycol molecular weights.

Examples of suitable second polymers are available commercially and include poly(ethylene-co-vinyl acetate) (pEVA) having vinyl acetate concentrations of between about 10% and about 50% (12%, 14%, 18%, 25%, 33% versions are commercially available), in the form of beads, pellets, granules, etc. pEVA co-polymers with lower percent vinyl acetate become increasingly insoluble in typical solvents, whereas those with higher percent vinyl acetate become decreasingly durable.

An exemplary polymer mixture for use in this invention includes mixtures of pBMA and pEVA. This mixture of polymers can be used with absolute polymer concentrations (i.e., the total combined concentrations of both polymers in the coating material), of between about 0.25 wt. % and about 99 wt. %. This mixture can also be used with individual polymer concentrations in the coating solution of between about 0.05 wt. % and about 99 wt. %. In one embodiment the polymer mixture includes pBMA with a molecular weight of from 100 kilodaltons to 900 kilodaltons and a pEVA copolymer with a vinyl acetate content of from 24 to 36 weight percent. In an embodiment the polymer mixture includes pBMA with a molecular weight of from 200 kilodaltons to 400 kilodaltons and a pEVA copolymer with a vinyl acetate content of from 24 to 36 weight percent. The concentration of the active agent or agents dissolved or suspended in the coating mixture can range from 0.01 to 99 percent, by weight, based on the weight of the final coating material.

Second polymers of the invention can also comprise one or more polymers selected from the group consisting of (i) poly(alkylene-co-alkyl(meth)acrylates, (ii) ethylene copolymers with other alkylenes, (iii) polybutenes, (iv) diolefin derived non-aromatic polymers and copolymers, (v) aromatic group-containing copolymers, and (vi) epichlorohydrin-containing polymers. First polymers of the invention can also comprise a polymer selected from the group consisting of poly(alkyl(meth)acrylates) and poly(aromatic (meth)acrylates), where "(meth)" will be understood by those skilled in the art to include such molecules in either the acrylic and/or methacrylic form (corresponding to the acrylates and/or methacrylates, respectively).

Poly(alkylene-co-alkyl(meth)acrylates) include those copolymers in which the alkyl groups are either linear or branched, and substituted or unsubstituted with non-interfering groups or atoms. Such alkyl groups can comprise from 1 to 8 carbon atoms, inclusive. Such alkyl groups can comprise from 1 to 4 carbon atoms, inclusive. In an embodiment, the alkyl group is methyl. In some embodiments, copolymers that include such alkyl groups can comprise from about 15% to about 80% (wt) of alkyl acrylate. When the alkyl group is methyl, the polymer contains from about 20% to about 40% methyl acrylate in some embodiments, and from about 25% to about 30% methyl acrylate in a particular embodiment. When the alkyl group is ethyl, the polymer contains from about 15% to about 40% ethyl acrylate in an embodiment, and when the alkyl group is butyl, the polymer contains from about 20% to about 40% butyl acrylate in an embodiment.

Alternatively, second polymers for use in this invention can comprise ethylene copolymers with other alkylenes, which in turn, can include straight and branched alkylenes, as well as substituted or unsubstituted alkylenes. Examples include copolymers prepared from alkylenes that comprise from 3 to 8 branched or linear carbon atoms, inclusive. In an embodiment, copolymers prepared from alkylene groups that comprise from 3 to 4 branched or linear carbon atoms, inclusive. In a particular embodiment, copolymers prepared from alkylene groups containing 3 carbon atoms (e.g., propene). By way of example, the other alkylene is a straight chain alkylene (e.g., 1-alkylene). Exemplary copolymers of this type can comprise from about 20% to about 90% (based on moles) of ethylene. In an embodiment, copolymers of this type comprise from about 35% to about 80% (mole) of ethylene. Such copolymers will have a molecular weight of between about 30 kilodaltons to about 500 kilodaltons. Exemplary copolymers are selected from the group consisting of poly(ethylene-co-propylene), poly(ethylene-co-1-butene), polyethylene-co-1-butene-co-1-hexene) and/or poly(ethylene-co-1-octene).

"Polybutenes" suitable for use in the present invention includes polymers derived by homopolymerizing or randomly interpolymerizing isobutylene, 1-butene and/or 2-butene. The polybutene can be a homopolymer of any of the isomers or it can be a copolymer or a terpolymer of any of the monomers in any ratio. In an embodiment, the polybutene contains at least about 90% (wt) of isobutylene or 1-butene. In a particular embodiment, the polybutene contains at least about 90% (wt) of isobutylene. The polybutene may contain non-interfering amounts of other ingredients or additives, for instance it can contain up to 1000 ppm of an antioxidant (e.g., 2,6-di-tert-butyl-methylphenol). By way of example, the polybutene can have a molecular weight between about 150 kilodaltons and about 1,000 kilodaltons. In an embodiment, the polybutene can have between about 200 kilodaltons and about 600 kilodaltons. In a particular embodiment, the polybutene can have between about 350 kilodaltons and about 500 kilodaltons. Polybutenes having a molecular weight greater than about 600 kilodaltons, including greater than 1,000 kilodaltons are available but are expected to be more difficult to work with.

Additional alternative second polymers include diolefin-derived, non-aromatic polymers and copolymers, including those in which the diolefin monomer used to prepare the polymer or copolymer is selected from butadiene ($CH_2$=CH—CH=$CH_2$) and/or isoprene ($CH_2$=CH—C($CH_3$)=$CH_2$). In an embodiment, the polymer is a homopolymer derived from diolefin monomers or is a copolymer of diolefin monomer with non-aromatic mono-olefin monomer, and optionally, the homopolymer or copolymer can be partially hydrogenated. Such polymers can be selected from the group consisting of polybutadienes prepared by the polymerization of cis-, trans- and/or 1,2-monomer units, or from a mixture of all three monomers, and polyisoprenes prepared by the polymerization of cis-1,4- and/or trans-1,4-monomer units. Alternatively, the polymer is a copolymer, including graft copolymers, and random copolymers based on a non-aromatic mono-olefin monomer such as acrylonitrile, and an alkyl (meth)acrylate and/or isobutylene. In an embodiment, when the mono-olefin monomer is acrylonitrile, the interpolymerized acrylonitrile is present at up to about 50% by weight; and when the mono-olefin monomer is isobutylene, the diolefin is isoprene (e.g., to form what is commercially known as a "butyl rubber"). Exemplary polymers and copolymers have a molecular weight between about 150 kilodaltons and about 1,000 kilodaltons. In an embodiment, polymers and copolymers have a molecular weight between about 200 kilodaltons and about 600 kilodaltons.

Additional alternative second polymers include aromatic group-containing copolymers, including random copolymers, block copolymers and graft copolymers. In an embodiment, the aromatic group is incorporated into the copolymer via the polymerization of styrene. In a particular embodiment, the random copolymer is a copolymer derived from copolymerization of styrene monomer and one or more monomers selected from butadiene, isoprene, acrylonitrile, a $C_1$-$C_4$ alkyl (meth)acrylate (e.g., methyl methacrylate) and/or butene. Useful block copolymers include copolymer containing (a) blocks of polystyrene, (b) blocks of an polyolefin selected from polybutadiene, polyisoprene and/or polybutene (e.g., isobutylene), and (c) optionally a third monomer (e.g., ethylene) copolymerized in the polyolefin block. The aromatic group-containing copolymers contain about 10% to about 50% (wt.) of polymerized aromatic monomer and the molecular weight of the copolymer is from about 300 kilodaltons to about 500 kilodaltons. In an embodiment, the molecular weight of the copolymer is from about 100 kilodaltons to about 300 kilodaltons.

Additional alternative second polymers include epichlorohydrin homopolymers and poly(epichlorohydrin-co-alkylene oxide) copolymers. In an embodiment, in the case of the copolymer, the copolymerized alkylene oxide is ethylene oxide. By way of example, epichlorohydrin content of the epichlorohydrin-containing polymer is from about 30% to 100% (wt). In an embodiment, epichlorohydrin content is from about 50% to 100% (wt). In an embodiment, the epichlorohydrin-containing polymers have a molecular weight from about 100 kilodaltons to about 300 kilodaltons.

In an embodiment, polymers of the invention include hydrophobic polymers. One method of defining the hydrophobicity of a polymer is by the solubility parameter (or Hildebrand parameter) of the polymer. The solubility parameter describes the attractive strength between molecules of the material. The solubility parameter is represented by Equation 1:

$$\delta = (\Delta E^v / V)^{1/2} \quad \text{(Equation 1)}$$

where $\delta$=solubility parameter $((cal/cm^3)^{1/2})$ $\Delta E^v$=energy of vaporization (cal)

V=molar volume $(cm^3)$

Solubility parameters cannot be calculated for polymers from heat of vaporization data because of their nonvolatility. Accordingly, solubility parameters must be calculated indirectly. One method involves identifying solvents in which a polymer dissolves without a change in heat or volume and then defining the solubility parameter of the polymer to be the same as the solubility parameters of the identified solvents. A more complete discussion of solubility parameters and methods of calculating the same can be found in Brandup et al., *Polymer Handbook*, 4th Ed., John Wiley & Sons, N.Y. (1999) beginning at VII p. 675.

As a general rule, the value of the solubility parameter $\delta$ is inversely proportional to the degree of hydrophobicity of a polymer. Thus, polymers that are very hydrophobic may have a low solubility parameter value. This general proposition is particularly applicable for polymers having a glass transition temperature below physiological temperature. In an embodiment, polymers used with the invention have a solubility parameter less than about 11.0 $(cal/cm^3)^{1/2}$. In an embodiment polymers used with the invention have a solubility parameter of less than about 10.0 $(cal/cm^3)^{1/2}$.

Polymers can also include a poly(ether ester) multiblock copolymer based on poly(ethylene glycol) (PEG) and poly(butylene terephthalate) and can be described by the following general structure:

[—($OCH_2CH_2$)$_n$—O—C(O)—$C_6H_4$—C(O)—]x[—O—($CH_2$)$_4$—O—C(O)—$C_6H_4$—C(O)—]y, where —$C_6H_4$— designates the divalent aromatic ring residue from each esterified molecule of terephthalic acid, n represents the number of ethylene oxide units in each hydrophilic PEG block, x represents the number of hydrophilic blocks in the copolymer, and y represents the number of hydrophobic blocks in the copolymer. n can be selected such that the molecular weight of the PEG block is between about 300 and about 4000. X and y can be selected so that the multiblock copolymer contains from about 55% up to about 80% PEG by weight.

The block copolymer can be engineered to provide a wide array of physical characteristics (e.g., hydrophilicity, adherence, strength, malleability, degradability, durability, flexibility) and active agent release characteristics (e.g., through controlled polymer degradation and swelling) by varying the values of n, x and y in the copolymer structure. Degradation of the copolymer does not create toxic degradation products or an acid environment, and its hydrophilic nature conserves the stability of labile active agents, such as proteins (e.g., lysozymes).

Polymers of the invention also include biodegradable polymers. Suitable biodegradable polymeric materials are selected from: (a) non-peptide polyamino polymers; (b) polyiminocarbonates; (c) amino acid-derived polycarbonates and polyarylates; and (d) poly(alkylene oxide) polymers. The biodegradable polymeric materials can break down to form degradation products that are non-toxic and do not cause a significant adverse reaction from the body.

In an embodiment, the biodegradable polymeric material is composed of a non-peptide polyamino acid polymer. Suitable non-peptide polyamino acid polymers are described, for example, in U.S. Pat. No. 4,638,045 ("Non-Peptide Polyamino Acid Bioerodible Polymers," Jan. 20, 1987). Generally speaking, these polymeric materials are derived from monomers, including two or three amino acid units having one of the following two structures illustrated below:

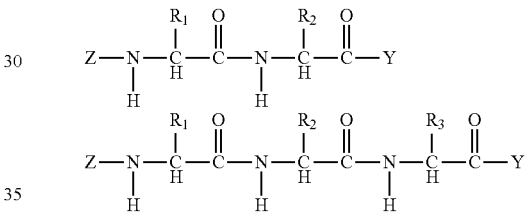

wherein the monomer units are joined via hydrolytically labile bonds at not less than one of the side groups $R_1$, $R_2$, and $R_3$, and where $R_1$, $R_2$, $R_3$ are the side chains of naturally occurring amino acids; Z is any desirable amine protecting group or hydrogen; and Y is any desirable carboxyl protecting group or hydroxyl. Each monomer unit comprises naturally occurring amino acids that are then polymerized as monomer units via linkages other than by the amide or "peptide" bond. The monomer units can be composed of two or three amino acids united through a peptide bond and thus comprise dipeptides or tripeptides. Regardless of the precise composition of the monomer unit, all are polymerized by hydrolytically labile bonds via their respective side chains rather than via the amino and carboxyl groups forming the amide bond typical of polypeptide chains. Such polymer compositions are nontoxic, are biodegradable, and can provide zero-order release kinetics for the delivery of active agents in a variety of therapeutic applications. According to these aspects, the amino acids are selected from naturally occurring L-alpha amino acids, including alanine, valine, leucine, isoleucine, proline, serine, threonine, aspartic acid, glutamic acid, asparagine, glutamine, lysine, hydroxylysine, arginine, hydroxyproline, methionine, cysteine, cystine, phenylalanine, tyrosine, tryptophan, histidine, citrulline, ornithine, lanthionine, hypoglycin A, β-alanine, γ-amino butyric acid, alpha aminoadipic acid, canavanine, venkolic acid, thiolhistidine, ergothionine, dihydroxyphenylalanine, and other amino acids well recognized and characterized in protein chemistry.

In an embodiment, the biodegradable polymeric material can be composed of polyiminocarbonates. Polyiminocarbonates are structurally related to polycarbonates, wherein imino groups (>C=NH) are present in the places normally occupied by carbonyl oxygen in the polycarbonates. Thus, the biodegradable component can be formed of polyiminocarbonates having linkages

For example, one useful polyiminocarbonate has the general polymer structural formula

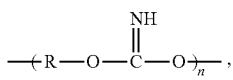

wherein R is an organic divalent group containing a non-fused aromatic organic ring, and n is greater than 1. Embodiments of the R group within the general formula above are exemplified by, but is not limited to the following:

R group

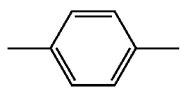

(a)

(b)

wherein R' is lower alkene $C_1$ to $C_6$

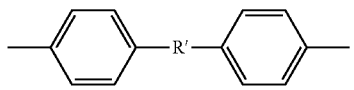

(c)

wherein n is an integer equal to or greater than 1, X is a hetero atom such as —O—, —S—, or a bridging group such as —NH—, —S(=O)—, —SO$_2$—, —C(=O)—, —C(CH$_3$)$_2$—, —CH(CH$_3$)—, —CH(CH$_3$)—CH$_2$— CH(CH$_3$)—, (d)

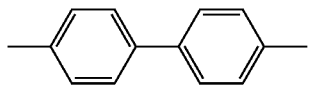

Also, compounds of the general formula

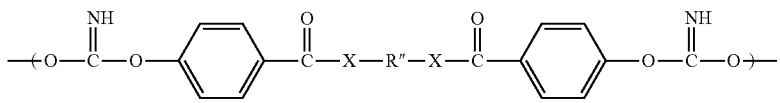

can be utilized, wherein X is O, NH, or NR'", wherein R'" is a lower alkyl radical; and R" is a divalent residue of a hydrocarbon including polymers such as a polyolefin, an oligoglycol or polyglycol such as polyalkylene glycol ether, a polyester, a polyurea, a polyamine, a polyurethane, or a polyamide. Exemplary starting material for use in accordance with these embodiments include diphenol compounds having the formula

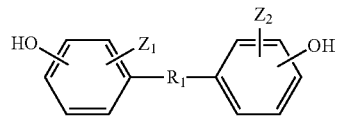

and dicyanate compounds having the

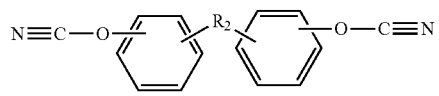

with $R_1$ and $R_2$ being the same or different and being alkylene, arylene, alkylarylene or a functional group containing heteroatoms. $Z_1$, and $Z_2$ can each represent one or more of the same or different radicals selected from the group consisting of hydrogen, halogen, lower-alkyl, carboxyl, amino, nitro, thioether, sulfoxide, and sulfonyl. Each of $Z_1$ and $Z_2$ can be hydrogen.

In an embodiment, the biodegradable polymeric material can be composed of various types of amino acid-derived polycarbonates and polyarylates. These amino acid-derived polycarbonates and polyarylates can be prepared by reacting certain amino acid-derived diphenol starting materials with either phosgene or dicarboxylic acids, respectively. Exemplary amino acid-derived diphenol starting materials for the preparation of the amino acid-derived polycarbonates and/or polyarylates of this embodiment are monomers that are capable of being polymerized to form polyiminocarbonates with glass transition temperatures ("Tg's") sufficiently low to permit thermal processing. The monomers according to this embodiment are diphenol compounds that are amino acid ester derivatives having the formula shown below:

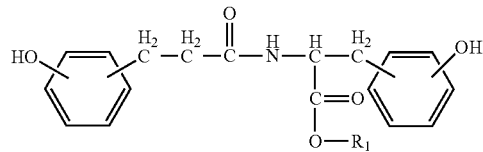

in which $R_1$ is an alkyl group containing up to 18 carbon atoms.

In yet another embodiment, the biodegradable polymeric material can be composed of copolymers containing both hydrophilic poly(alkylene oxides) (PAO) and biodegradable sequences, wherein the hydrocarbon portion of each PAO unit contains from 1 to 4 carbon atoms, or 2 carbon atoms (i.e., the PAO is poly(ethylene oxide)). For example, useful biodegradable polymeric materials can be made of block copolymers containing PAO and amino acids or peptide sequences and contain one or more recurring structural units independently represented by the structure -L-R$_1$-L-R$_2$—, wherein R$_1$ is a poly(alkylene oxide), L is —O— or —NH—, and R$_2$ is an amino acid or peptide sequence containing two carboxylic acid groups and at least one pendent amino group.

Other useful biodegradable polymeric materials are composed of polyarylate or polycarbonate random block copolymers that include tyrosine-derived diphenol monomers and poly(alkylene oxide), such as the polycarbonate shown below:

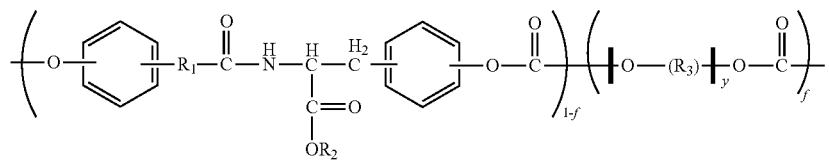

wherein R$_1$ is —CH=CH— or (—CH$_2$—)$_j$, in which j is 0 to 8; R$_2$ is selected from straight and branched alkyl and alkylaryl groups containing up to 18 carbon atoms and optionally containing at least one ether linkage, and derivatives of biologically and pharmaceutically active compounds covalently bonded to the copolymer; each R$_3$ is independently selected from alkylene groups containing 1 to 4 carbon atoms; y is between 5 and about 3000; and f is the percent molar fraction of alkylene oxide in the copolymer and ranges from about 0.01 to about 0.99.

In some embodiments, pendent carboxylic acid groups can be incorporated within the polymer bulk for polycarbonates, polyarylates, and/or poly(alkylene oxide) block copolymers thereof, to further control the rate of polymer backbone degradation and resorption.

Polymers used in embodiments of the invention can include polymers that are components of elution control coatings. By way of example, U.S. Pat. No. 6,214,901 (Chudzik et al.) discloses polymers used in bioactive agent release coatings, the contents of which is herein incorporated by reference.

Active Agents

Coating solutions used with methods of the invention can contain one or more active agents. As used herein, the term "active agent" means a compound that has a particular desired activity. For example, an active agent can be a therapeutic compound that exerts a specific activity on a subject. In some embodiments, active agent will, in turn, refer to a peptide, protein, carbohydrate, nucleic acid, lipid, polysaccharide or combinations thereof, or synthetic inorganic or organic molecule, that causes a desired biological effect when administered in vivo to an animal, including but not limited to birds and mammals, including humans. In some embodiments, the active agent can be a bioactive agent. Active agents can have many different types of elution profiles.

Active agents useful according to the invention include substances that possess desirable therapeutic characteristics for application to the implantation site. Active agents useful in the present invention can include many types of therapeutics including thrombin inhibitors, antithrombogenic agents, thrombolytic agents, fibrinolytic agents, anticoagulants, anti-platelet agents, vasospasm inhibitors, calcium channel blockers, steroids, vasodilators, anti-hypertensive agents, antimicrobial agents, antibiotics, antibacterial agents, antiparasite and/or antiprotozoal solutes, antiseptics, antifungals, angiogenic agents, anti-angiogenic agents, inhibitors of surface glycoprotein receptors, antimitotics, microtubule inhibitors, antisecretory agents, actin inhibitors, remodeling inhibitors, antisense nucleotides, anti-metabolites, miotic agents, anti-proliferatives, anticancer chemotherapeutic agents, anti-neoplastic agents, antipolymerases, antivirals, anti-AIDS substances, anti-inflammatory steroids or non-steroidal anti-inflammatory agents, analgesics, antipyretics, immunosuppressive agents, immunomodulators, growth hormone antagonists, growth factors, radiotherapeutic agents, peptides, proteins, enzymes, extracellular matrix components, ACE inhibitors, free radical scavengers, chelators, anti-oxidants, photodynamic therapy agents, gene therapy agents, anesthetics, immunotoxins, neurotoxins, opioids, dopamine agonists, hypnotics, antihistamines, tranquilizers, anticonvulsants, muscle relaxants and anti-Parkinson substances, antispasmodics and muscle contractants, anticholinergics, ophthalmic agents, antiglaucoma solutes, prostaglandins, antidepressants, antipsychotic substances, neurotransmitters, anti-emetics, imaging agents, specific targeting agents, and cell response modifiers.

More specifically, in embodiments the active agent can include heparin, covalent heparin, synthetic heparin salts, or another thrombin inhibitor; hirudin, hirulog, argatroban, D-phenylalanyl-L-poly-L-arginyl chloromethyl ketone, or another antithrombogenic agent; urokinase, streptokinase, a tissue plasminogen activator, or another thrombolytic agent; a fibrinolytic agent; a vasospasm inhibitor; a calcium channel blocker, a nitrate, nitric oxide, a nitric oxide promoter, nitric oxide donors, dipyridamole, or another vasodilator; HYTRIN® or other antihypertensive agents; a glycoprotein IIb/IIIa inhibitor (abciximab) or another inhibitor of surface glycoprotein receptors; aspirin, ticlopidine, clopidogrel or another antiplatelet agent; colchicine or another antimitotic, or another microtubule inhibitor; dimethyl sulfoxide (DMSO), a retinoid, or another anti secretory agent; cytochalasin or another actin inhibitor; cell cycle inhibitors; remodeling inhibitors; deoxyribonucleic acid, an antisense nucleotide, or another agent for molecular genetic intervention; methotrexate, or another antimetabolite or antiproliferative agent; tamoxifen citrate, TAXOL®, paclitaxel, or the derivatives thereof, rapamycin (or other rapalogs e.g. ABT-578 or sirolimus), vinblastine, vincristine, vinorelbine, etoposide, tenopiside, dactinomycin (actinomycin D), daunorubicin, doxorubicin, idarubicin, anthracyclines, mitoxantrone, bleomycin, plicamycin (mithramycin), mitomycin, mechlorethamine, cyclophosphamide and its analogs, chlorambucil, ethylenimines, methylmelamines, alkyl sulfonates (e.g., busulfan), nitrosoureas (carmustine, etc.), streptozocin, methotrexate (used with many indications), fluorouracil, floxuridine, cytarabine, mercaptopurine, thioguanine, pentostatin, 2-chlorodeoxyadenosine, cisplatin, carboplatin, procarbazine, hydroxyurea, morpholino phosphorodiamidate oligomer or other anti-cancer chemotherapeutic agents; cyclosporin, tacrolimus (FK-506), pimecrolimus, azathioprine, mycophenolate mofetil, mTOR inhibitors, or another immunosuppressive agent; cortisol, cortisone, dexamethasone, dexamethasone sodium phosphate, dexamethasone acetate, dexamethasone derivatives, betamethasone, fludrocortisone, prednisone, prednisolone, 6U-methylprednisolone, triamcinolone (e.g., triamcinolone acetonide), or another steroidal agent; trapidil (a PDGF antagonist), angiopeptin (a growth hormone antagonist), angiogenin, a growth factor (such as vascular endothelial growth factor (VEGF)), or an anti-growth factor antibody (e.g., ranibizumab, which is sold under the tradename LUCENTIS®), or another growth factor antagonist or agonist; dopamine, bromocriptine mesylate, pergolide mesylate, or another dopamine agonist; $^{60}$Co (5.3 year half life), $^{192}$Ir (73.8 days), $^{32}$P (14.3 days), (68 hours), $^{90}$Y (64 hours), $^{99}$Tc (6 hours), or another radiotherapeutic agent; iodine-containing compounds, barium-containing compounds, gold, tantalum, platinum, tungsten or another heavy metal functioning as a radiopaque agent; a peptide, a protein, an extracellular matrix component, a cellular component or another biologic agent; captopril, enalapril or another angiotensin converting enzyme (ACE) inhibitor; angiotensin receptor blockers; enzyme inhibitors (including growth factor signal transduction kinase inhibitors); ascorbic acid, alpha tocopherol, superoxide dismutase, deferoxamine, a 21-aminosteroid (lasaroid) or another free radical scavenger, iron chelator or antioxidant; a $^{14}$C-, $^{3}$H-, $^{131}$I, $^{32}$P- or $^{36}$S-radiolabelled form or other radiolabelled form of any of the foregoing; an estrogen (such as estradiol, estriol, estrone, and the like) or another sex hormone; AZT or other antipolymerases; acyclovir, famciclovir, rimantadine hydrochloride, ganciclovir sodium, Norvir, Crixivan, or other antiviral agents; 5-aminolevulinic acid, meta-tetrahydroxyphenylchlorin, hexadecafluorozinc phthalocyanine, tetramethyl hematoporphyrin, rhodamine 123 or other photodynamic therapy agents; an IgG2 Kappa antibody against Pseudomonas aeruginosa exotoxin A and reactive with A431 epidermoid carcinoma cells, monoclonal antibody against the noradrenergic enzyme dopamine beta-hydroxylase conjugated to saporin, or other antibody targeted therapy agents; gene therapy agents; enalapril and other prodrugs; PRO SCAR®, HYTRIN® or other agents for treating benign prostatic hyperplasia (BHP); mitotane, aminoglutethimide, breveldin, acetaminophen, etodalac, tolmetin, ketorolac, ibuprofen and derivatives, mefenamic acid, meclofenamic acid, piroxicam, tenoxicam, phenylbutazone, oxyphenbutazone, nabumetone, auranofin, aurothioglucose, gold sodium thiomalate, a mixture of any of these, or derivatives of any of these.

Other biologically useful compounds that can also be included in the coating include, but are not limited to, hormones, β-blockers, anti-anginal agents, cardiac inotropic agents, corticosteroids, analgesics, anti-inflammatory agents, anti-arrhythmic agents, immunosuppressants, anti-bacterial agents, anti-hypertensive agents, anti-malarials, anti-neoplastic agents, anti-protozoal agents, anti-thyroid agents, sedatives, hypnotics and neuroleptics, diuretics, anti-parkinsonian agents, gastro-intestinal agents, anti-viral agents, anti-diabetics, anti-epileptics, anti-fungal agents, histamine H-receptor antagonists, lipid regulating agents, muscle relaxants, nutritional agents such as vitamins and minerals, stimulants, nucleic acids, polypeptides, and vaccines.

Antibiotics are substances which inhibit the growth of or kill microorganisms. Antibiotics can be produced synthetically or by microorganisms. Examples of antibiotics include penicillin, tetracycline, chloramphenicol, minocycline, doxycycline, vancomycin, bacitracin, kanamycin, neomycin, gentamycin, erythromycin, geldanamycin, geldanamycin analogs, cephalosporins, or the like. Examples of cephalosporins include cephalothin, cephapirin, cefazolin, cephalexin, cephradine, cefadroxil, cefamandole, cefoxitin, cefaclor, cefuroxime, cefonicid, ceforanide, cefotaxime, moxalactam, ceftizoxime, ceftriaxone, and cefoperazone.

Antiseptics are recognized as substances that prevent or arrest the growth or action of microorganisms, generally in a nonspecific fashion, e.g., either by inhibiting their activity or destroying them. Examples of antiseptics include silver sulfadiazine, chlorhexidine, glutaraldehyde, peracetic acid, sodium hypochlorite, phenols, phenolic compounds, iodophor compounds, quaternary ammonium compounds, and chlorine compounds.

Antiviral agents are substances capable of destroying or suppressing the replication of viruses. Examples of anti-viral agents include α-methyl-1-adamantanemethylamine, hydroxy-ethoxymethylguanine, adamantanamine, 5-iodo-2'-deoxyuridine, trifluorothymidine, interferon, and adenine arabinoside.

Enzyme inhibitors are substances that inhibit an enzymatic reaction. Examples of enzyme inhibitors include edrophonium chloride, N-methylphysostigmine, neostigmine bromide, physostigmine sulfate, tacrine HCL, tacrine, 1-hydroxy maleate, iodotubercidin, p-bromotetramisole, 10-(α-diethylaminopropionyl)-phenothiazine hydrochloride, calmidazolium chloride, hemicholinium-3,3,5-dinitrocatechol, diacylglycerol kinase inhibitor I, diacylglycerol kinase inhibitor II, 3-phenylpropargylaminie, N-monomethyl-L-arginine acetate, carbidopa, 3-hydroxybenzylhydrazine HCl, hydralazine HCl, clorgyline HCl, deprenyl HCl L(-), deprenyl HCl D(+), hydroxylamine HCl, iproniazid phosphate, 6-MeO-tetrahydro-9H-pyrido-indole, nialamide, pargyline HCl, quinacrine HCl, semicarbazide HCl, tranylcypromine HCl, N,N-diethylaminoethyl-2,2-di-phenylvalerate hydrochloride, 3-isobutyl-1-methylxanthne, papaverine HCl, indomethacine, 2-cyclooctyl-2-hydroxyethylamine hydrochloride, 2,3-dichloro-α-methylbenzylamine (DCMB), 8,9-dichloro-2,3,4,5-tetrahydro-1H-2-benzazepine hydrochloride, p-aminoglutethimide, p-aminoglutethimide tartrate R(+), p-aminoglutethimide tartrate S(-), 3-iodotyrosine, alpha-methyltyrosine L(-), alpha-methyltyrosine D(-), cetazolamide, dichlorphenamide, 6-hydroxy-2-benzothiazolesulfonamide, and allopurinol.

Anti-pyretics are substances capable of relieving or reducing fever. Anti-inflammatory agents are substances capable of counteracting or suppressing inflammation. Examples of such agents include aspirin (salicylic acid), indomethacin, sodium indomethacin trihydrate, salicylamide, naproxen, colchicine, fenoprofen, sulindac, diflunisal, diclofenac, indoprofen and sodium salicylamide.

Local anesthetics are substances that have an anesthetic effect in a localized region. Examples of such anesthetics include procaine, lidocaine, tetracaine and dibucaine.

Imaging agents are agents capable of imaging a desired site, e.g., tumor, in vivo. Examples of imaging agents include substances having a label that is detectable in vivo, e.g., antibodies attached to fluorescent labels. The term antibody includes whole antibodies or fragments thereof.

Cell response modifiers are chemotactic factors such as platelet-derived growth factor (PDGF). Other chemotactic factors include neutrophil-activating protein, monocyte chemoattractant protein, macrophage-inflammatory protein, SIS (small inducible secreted), platelet factor, platelet basic protein, melanoma growth stimulating activity, epidermal growth factor, transforming growth factor alpha, fibroblast growth factor, platelet-derived endothelial cell growth factor, insulin-like growth factor, nerve growth factor, bone growth/cartilage-inducing factor (alpha and beta), and matrix metalloproteinase inhibitors. Other cell response modifiers are the interleukins, interleukin receptors, interleukin inhibitors, interferons, including alpha, beta, and gamma; hematopoietic factors, including erythropoietin, granulocyte colony stimulating factor, macrophage colony stimulating factor and granulocyte-macrophage colony stimulating factor; tumor necrosis factors, including alpha and beta; transforming growth factors (beta), including beta-1, beta-2, beta-3, inhibin, activin, and DNA that encodes for the production of any of these proteins, antisense molecules, androgenic receptor blockers and statin agents.

In an embodiment, the active agent used with the invention includes compounds having a steroid ring system. Compounds having a steroid ring system can be referred to as steroids. In an embodiment, the active agent is a steroid. Steroids include both naturally occurring compounds and synthetic analogues based on the cyclopenta[a]phenanthrene carbon skeleton, partially or completely hydrogenated. Steroids can include glucocorticoids, estrogens and androgens. By way of example, steroids can include dexamethasone, dexamethasone acetate, dexamethasone sodium phosphate, cortisone, cortisone acetate, hydrocortisone, hydrocortisone acetate, hydrocortisone cypionate, hydrocortisone sodium phosphate, hydrocortisone sodium succinate, prednisone, prednisolone, prednisolone acetate, prednisolone sodium phosphate, prednisolone tebutate, prednisolone pivalate, triamcinolone, triamcinolone acetonide, triamcinolone hexacetonide, triamcinolone diacetate, methylprednisolone, methylprednisolone acetate, methylprednisolone sodium succinate, flunsolide, beclomethasone dipropionate, betamethasone sodium phosphate, betamethasone, vetamethasone disodium phosphate, vetamethasone sodium phosphate, betamethasone acetate, betamethasone di sodium phosphate, chloroprednisone acetate, corticosterone, desoxycorticosterone, desoxycorticosterone acetate, desoxycorticosterone pivalate, desoximethasone, estradiol, fludrocortisone, fludrocortisone acetate, dichlorisone acetate, fluorohydrocortisone, fluorometholone, fluprednisolone, paramethasone, paramethasone acetate, androsterone, fluoxymesterone, aldosterone, methandrostenolone, methylandrostenediol, methyl testosterone, norethandrolone, testosterone, testosterone enanthate, testosterone propionate, equilenin, equilin, estradiol benzoate, estradiol dipropionate, estriol, estrone, estrone benzoate, acetoxypregnenolone, anagestone acetate, chlormadinone acetate, flurogestone acetate, hydroxymethylprogesterone, hydroxymethylprogesterone acetate, hydroxyprogesterone, hydroxyprogesterone acetate, hydroxyprogesterone caproate, melengestrol acetate, normethisterone, pregnenolone, progesterone, ethynyl estradiol, mestranol, dimethisterone, ethisterone, ethynodiol diacetate, norethindrone, norethindrone acetate, norethisterone, fluocinolone acetonide, flurandrenolone, hydrocortisone sodium succinate, methylprednisolone sodium succinate, prednisolone phosphate sodium, triamcinolone acetonide, hydroxydione sodium, spironolactone, oxandrolone, oxymetholone, prometholone, testosterone cypionate, testosterone phenylacetate, estradiol cypionate, and norethynodrel, analogs thereof, or combinations thereof.

Active agents used with the invention can include macromolecules, small molecules, hydrophilic molecules, hydrophobic molecules, and the like. Macromolecular active agents used with embodiments of the invention can include proteins, nucleic acids, and polysaccharides. By way of example, proteins can include glycosylated proteins, antibodies (both monoclonal and polyclonal), antibody derivatives (including diabodies, f(ab) fragments, humanized antibodies, etc.), cytokines, growth factors, receptor ligands, enzymes, and the like. Nucleic acids can include RNA, DNA, cDNA, and the like.

In an embodiment, macromolecular active agents used with the invention have a molecular weight (or average molecular weight) of greater than about 10 kD (1 kilodalton is equal to 1,000 atomic mass units). In an embodiment, the macromolecular active agent includes a protein of greater than about 10 kD. In an embodiment, the macromolecular active agent includes a protein of greater than about 100 kD.

In some embodiments, the active agent of the coating can include agents that are small molecules. In some embodiments, the active agent can include therapeutic agents that are hydrophilic small molecules. In some embodiments, the active agent can include therapeutic agents that are hydrophobic small molecules. As used herein, small molecules can include those with a molecular weight of equal to or less than 10 kilodaltons. In an embodiment, small molecules have a molecular weight of less than about 5 kilodaltons.

By way of example, small molecule active agents can include Trigonelline HCL, diclofenac, and chlorhexidine diacetate. Small molecules can include many types of therapeutics including those as described above with respect to macromolecules (e.g., thrombin inhibitors, antithrombogenic agents, etc.).

The weight of the coating attributable to the active agent can be in any range desired for a given active agent in a given application. In some embodiments, weight of the coating attributable to the active agent is in the range of about 1 microgram to about 10 milligrams of active agent per $cm^2$ of the effective surface area of the device. By "effective" surface area it is meant the surface amenable to being coated with the composition itself. For a flat, nonporous, surface, for instance, this will generally be the macroscopic surface area itself, while for considerably more porous or convoluted (e.g., corrugated, pleated, or fibrous) surfaces the effective surface area can be significantly greater than the corresponding macroscopic surface area. In an embodiment, the weight of the coating attributable to the active agent is between about 0.01 mg and about 0.5 mg of active agent per $cm^2$ of the gross surface area of the device. In an embodiment, the weight of the coating attributable to the active agent is greater than about 0.01 mg.

In some embodiments, more than one active agent can be used as a part of the coating material. Specifically, co-agents or co-drugs can be used. A co-agent or co-drug can act differently than the first agent or drug. The co-agent or co-drug can have an elution profile that is different than the first agent or drug. In some embodiments, accessory agents are included such as chaperonins.

Devices

Embodiments of the invention can be used to coat many different types of devices including medical devices. Medical devices can include both implantable devices and non-implantable medical devices.

Embodiments of the invention can be used with implantable, or transitorily implantable, devices including, but not limited to, vascular devices such as grafts (e.g., abdominal aortic aneurysm grafts, etc.), stents (e.g., self-expanding stents typically made from nitinol, balloon-expanded stents typically prepared from stainless steel, degradable coronary stents, etc.), catheters (including arterial, intravenous, blood pressure, stent graft, etc.), valves (e.g., polymeric or carbon mechanical valves, tissue valves, valve designs including percutaneous, sewing cuff, and the like), embolic protection filters (including distal protection devices), vena cava filters, aneurysm exclusion devices, artificial hearts, cardiac jackets, and heart assist devices (including left ventricle assist devices), implantable defibrillators, electro-stimulation devices and leads (including pacemakers, lead adapters and lead connectors), implanted medical device power supplies (e.g., batteries, etc.), peripheral cardiovascular devices, atrial septal defect closures, left atrial appendage filters, valve annuloplasty devices (e.g., annuloplasty rings), mitral valve repair devices, vascular intervention devices, ventricular assist pumps, and vascular access devices (including parenteral feeding catheters, vascular access ports, central venous access catheters); surgical devices such as sutures of all types, staples, anastomosis devices (including anastomotic closures), suture anchors, hemostatic barriers, screws, plates, clips, vascular implants, tissue scaffolds, cerebrospinal fluid shunts, shunts for hydrocephalus, drainage tubes, catheters including thoracic cavity suction drainage catheters, abscess drainage catheters, biliary drainage products, and implantable pumps; orthopedic devices such as joint implants, acetabular cups, patellar buttons, bone repair/augmentation devices, spinal devices (e.g., vertebral disks and the like), bone pins, cartilage repair devices, and artificial tendons; dental devices such as dental implants and dental fracture repair devices; drug delivery devices such as drug delivery pumps, implanted drug infusion tubes, drug infusion catheters, and intravitreal drug delivery devices; ophthalmic devices including orbital implants, glaucoma drain shunts and intraocular lenses; urological devices such as penile devices (e.g., impotence implants), sphincter, urethral, prostate, and bladder devices (e.g., incontinence devices, benign prostate hyperplasia management devices, prostate cancer implants, etc.), urinary catheters including indwelling ("Foley") and non-indwelling urinary catheters, and renal devices; synthetic prostheses such as breast prostheses and artificial organs (e.g., pancreas, liver, lungs, heart, etc.); respiratory devices including lung catheters; neurological devices such as neurostimulators, neurological catheters, neurovascular balloon catheters, neuro-aneurysm treatment coils, and neuropatches; ear nose and throat devices such as nasal buttons, nasal and airway splints, nasal tampons, ear wicks, ear drainage tubes, tympanostomy vent tubes, otological strips, laryngectomy tubes, esophageal tubes, esophageal stents, laryngeal stents, salivary bypass tubes, and tracheostomy tubes; biosensor devices including glucose sensors, cardiac sensors, intra-arterial blood gas sensors; oncological implants; and pain management implants.

Classes of suitable non-implantable devices can include dialysis devices and associated tubing, catheters, membranes, and grafts; autotransfusion devices; vascular and surgical devices including atherectomy catheters, angiographic catheters, intraaortic balloon pumps, intracardiac suction devices, blood pumps, blood oxygenator devices (including tubing and membranes), blood filters, blood temperature monitors, hemoperfusion units, plasmapheresis units, transition sheaths, dialators, intrauterine pressure devices, clot extraction catheters, percutaneous transluminal angioplasty catheters, electrophysiology catheters, breathing circuit connectors, stylets (vascular and non-vascular), coronary guide wires, peripheral guide wires; dialators (e.g., urinary, etc.); surgical instruments (e.g. scalpels and the like); endoscopic devices (such as endoscopic surgical tissue extractors, esophageal stethoscopes); and general medical and medically related devices including blood storage bags, umbilical tape, membranes, gloves, surgical drapes, wound dressings, wound management devices, needles, percutaneous closure devices, transducer protectors, pessary, uterine bleeding patches, PAP brushes, clamps (including bulldog clamps), cannulae, cell culture devices, materials for in vitro diagnostics, chromatographic support materials, infection control devices, colostomy bag attachment devices, birth control devices; disposable temperature probes; and pledgets.

In some aspects, embodiments of the invention can be utilized in connection with ophthalmic devices. Suitable ophthalmic devices in accordance with these aspects can provide bioactive agent to any desired area of the eye. In some aspects, the devices can be utilized to deliver bioactive agent to an anterior segment of the eye (in front of the lens), and/or a posterior segment of the eye (behind the lens). Suitable ophthalmic devices can also be utilized to provide bioactive agent to tissues in proximity to the eye, when desired.

In some aspects, embodiments of the invention can be utilized in connection with ophthalmic devices configured for placement at an external or internal site of the eye. Suitable external devices can be configured for topical administration of bioactive agent. Such external devices can reside on an external surface of the eye, such as the cornea (for example, contact lenses) or bulbar conjunctiva. In some embodiments, suitable external devices can reside in proximity to an external surface of the eye.

Devices configured for placement at an internal site of the eye can reside within any desired area of the eye. In some aspects, the ophthalmic devices can be configured for placement at an intraocular site, such as the vitreous. Illustrative intraocular devices include, but are not limited to, those described in U.S. Pat. No. 6,719,750 B2 ("Devices for Intraocular Drug Delivery," Varner et al.) and U.S. Pat. No. 5,466,233 ("Tack for Intraocular Drug Delivery and Method for Inserting and Removing Same," Weiner et al.); U.S. Publication Nos. 2005/0019371 A1 ("Controlled Release Bioactive Agent Delivery Device," Anderson et al.), 2004/0133155 A1 ("Devices for Intraocular Drug Delivery," Varner et al.), 2005/0059956 A1 ("Devices for Intraocular Drug Delivery," Varner et al.), and 2003/0014036 A1 ("Reservoir Device for Intraocular Drug Delivery," Varner et al.); and U.S. application Ser. No. 11/204,195 (filed Aug. 15, 2005, Anderson et al.), Ser. No. 11/204,271 (filed Aug. 15, 2005, Anderson et al.), Ser. No. 11/203,981 (filed Aug. 15, 2005, Anderson et al.), Ser. No. 11/203,879 (filed Aug. 15, 2005, Anderson et al.), Ser. No. 11/203,931 (filed Aug. 15, 2005, Anderson et al.); and related applications.

In some aspects, the ophthalmic devices can be configured for placement at a subretinal area within the eye. Illustrative ophthalmic devices for subretinal application include, but are not limited to, those described in U.S. Patent Publication No. 2005/0143363 ("Method for Subretinal Administration of Therapeutics Including Steroids; Method for Localizing Pharmacodynamic Action at the Choroid and the Retina; and Related Methods for Treatment and/or Prevention of Retinal Diseases," de Juan et al.); U.S. application Ser. No. 11/175,850 ("Methods and Devices for the Treatment of Ocular Conditions," de Juan et al.); and related applications.

Suitable ophthalmic devices can be configured for placement within any desired tissues of the eye. For example, ophthalmic devices can be configured for placement at a subconjunctival area of the eye, such as devices positioned extrasclerally but under the conjunctiva, such as glaucoma drainage devices and the like.

The present invention may be better understood with reference to the following examples. These examples are intended to be representative of specific embodiments of the invention, and are not intended as limiting the scope of the invention.

EXAMPLES

Example 1: Preparation of Coating Solutions Saturated/Unsaturated

Coating solutions were prepared with various concentrations of drug, polymers, and solvents. Specifically, five different coating solutions were prepared as follows (the coating solutions are summarized in Table 1 below):

Solution 1: Estradiol was combined with THF (tetrahydrofuran) to form an active agent solution. PEVA (polyethylene-co-vinyl acetate, 33% vinyl acetate) and PBMA (poly-n-butyl methacrylate) were combined with toluene to form a polymer solution. The active agent solution and the toluene solution were combined to form a coating solution having 40 mg/ml total solids including 30 wt. % estradiol, 20 wt. % PEVA, and 50 wt. % PBMA in a solvent of 80% toluene and 20% THF (four parts toluene to one part THF). The coating solution was allowed to stand for a period of minutes at ambient temperature and was observed to be clear, indicating that the estradiol was at a soluble concentration for this solvent composition.

Solution 2: Estradiol was combined with THF (tetrahydrofuran) to form an active agent solution. PEVA (polyethylene-co-vinyl acetate, 33% vinyl acetate) and PBMA (poly-n-butyl methacrylate) were combined with toluene to form a polymer solution. The active agent solution and the toluene solution were combined to form a coating solution having 40 mg/ml total solids including 30 wt. % estradiol, 20 wt. % PEVA, and 50 wt. % PBMA in a solvent of 85% toluene and 15% THF. The coating solution was allowed to stand for a period of minutes at ambient temperature and crystal formation was observed, indicating that the estradiol was at a concentration exceeding solubility limits for this solvent composition.

Solution 3: Estradiol was combined with THF (tetrahydrofuran) to form an active agent solution. PEVA (polyethylene-co-vinyl acetate, 33% vinyl acetate) and PBMA (poly-n-butyl methacrylate) were combined with toluene to form a polymer solution. The active agent solution and the toluene solution were combined to form a coating solution having 40 mg/ml total solids including 40 wt. % estradiol, 20 wt. % PEVA, and 40 wt. % PBMA in a solvent of 80% toluene and 20% THF. The coating solution was allowed to stand for a period of minutes at ambient temperature and crystal formation was observed, indicating that the estradiol was at a concentration exceeding solubility limits for this solvent composition.

Solution 4: Estradiol was combined with THF (tetrahydrofuran) to form an active agent solution. PEVA (polyethylene-co-vinyl acetate, 33% vinyl acetate) and PBMA (poly-n-butyl methacrylate) were combined with toluene to form a polymer solution. The active agent solution and the polymer solution were combined to form a coating solution having 40 mg/ml total solids including 35 wt. % estradiol, 20 wt. % PEVA, and 45 wt. % PBMA in a solvent of 80% toluene and 20% THF. The coating solution was allowed to stand for a period of minutes at ambient temperature and crystal formation was observed, indicating that the estradiol was at a concentration exceeding solubility limits for this solvent composition.

Solution 5: Estradiol was combined with THF (tetrahydrofuran) to form an active agent solution. PEVA (polyethylene-co-vinyl acetate, 33% vinyl acetate) and PBMA (poly-n-butyl methacrylate) were combined with toluene to form a polymer solution. The active agent solution and the toluene solution were combined to form a coating solution having 40 mg/ml total solids including 32.5 wt. % estradiol, 20 wt. % PEVA, and 47.5 wt. % PBMA in a solvent of 80% toluene and 20% THF. The coating solution was allowed to stand for a period of minutes at ambient temperature and the start of a small amount of crystal formation was observed, indicating that the estradiol was at a concentration slightly exceeding solubility limits for this solvent composition.

TABLE 1

| | Solids (40 mg/ml) | | | Solvent | | |
|---|---|---|---|---|---|---|
| Solution | Estradiol (wt. %) | PEVA (wt. %) | PBMA (wt. %) | toluene | THF | Result |
| 1 | 30.0 | 20.0 | 50.0 | 80 | 20 | no crystals |
| 2 | 30.0 | 20.0 | 50.0 | 85 | 15 | many crystals |
| 3 | 40.0 | 20.0 | 40.0 | 80 | 20 | many crystals |
| 4 | 35.0 | 20.0 | 45.0 | 80 | 20 | many crystals |
| 5 | 32.5 | 20.0 | 47.5 | 80 | 20 | some crystals |

This example demonstrates that at a total solids concentration of 40 mg/ml the solubility limit of estradiol is somewhere between 30.0 wt. % and 32.5 wt. % at ambient temperature (approximately 21-22° C.) for a solvent including 80% toluene and 20% THF. This is equivalent to a solubility limit of between about 12 mg/ml and about 13 mg/ml of estradiol in a solvent including 80% toluene and 20% THF in the presence of PEVA and PBMA.

Example 2: Non-Saturated Coating Composition with THF/IPA Solvent

Estradiol, polyethylene-co-vinyl acetate (PEVA) (33% vinyl acetate), and poly-n-butyl methacrylate (PBMA) were combined in equal weight proportions in a solution that was 90% tetrahydrofuran (THF) and 10% isopropyl alcohol (IPA). The resulting solution had a total solids concentration of 40 mg/ml (33% PEVA/33% PBMA/33% estradiol). The resulting solution was below the saturation point for estradiol in a solvent of 90% THF/10% IPA at ambient temperature (approximately 21-22° C.).

A stainless steel stent 18 mm in length was obtained and prepared by first applying a layer of parylene C using a vapor-deposition technique. After the parylene was disposed onto the stent, the coating solution was applied to the stent using an ultrasonic spray technique at a relative humidity of 10%. Ultrasonic spray techniques are disclosed in U.S. Published Application 2004/0062875 (Chappa et al.) the contents of which are herein incorporated by reference. A total coating weight of 657 μg was applied to the stent (measured after the solvent had substantially evaporated off) resulting in a drug loading of approximately 217 μg of estradiol.

Figure 2:
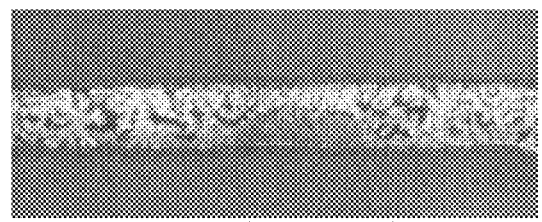
FIG. 2 is a microscopic view of a coating on a device of FIG. 1 taken under polarizing light four days later.

On day 0 (the day the coating was applied), optical microscopy was used with polarized light to evaluate the surface of the stent. The polarized light image shows the formation of crystals of active agent not just at the surface of the coating but throughout the coating thickness. FIG. 1 shows the coating at Day 0. It was estimated that approximately 50% of the coating contained active agent crystals. On day 4, optical microscopy was again used with polarized light to evaluate the coating. FIG. 2 shows the stent surface at Day 4. It was estimated that approximately 95% of coating contained active agent crystals.

Figure 3:
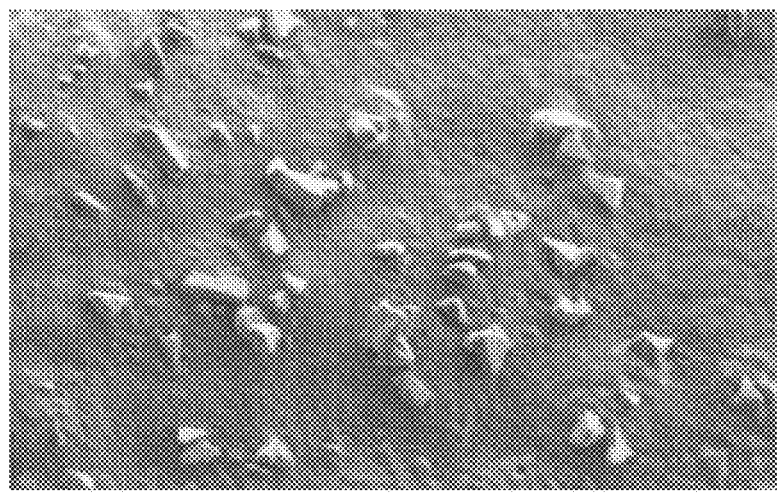
FIG. 3 is an image of the surface features of a coating on a device taken using scanning electron microscopy (SEM).

After 7 days, the surface of the stent was examined using scanning electron microscopy (SEM) at various magnifications. A 7500× view is shown in FIG. 3. SEM analysis revealed that there were significant quantities of active agent crystals coming out of the surface of the coating.

This example shows that when a coating solution is applied wherein the concentration of the active agent is below the saturation point, the crystallization process may take place over an extended period of time.

Example 3: Non-Saturated Coating Composition with Chloroform/Methanol Solvent

Estradiol, polyethylene-co-vinyl acetate (PEVA) (33% vinyl acetate), and poly-n-butyl methacrylate (PBMA) were combined in equal weight proportions in a solution that was 80% chloroform and 20% methanol. The resulting solution had a total solids concentration of 40 mg/ml (33% PEVA/33% PBMA/33% estradiol). The resulting solution was below the saturation point for estradiol in a solvent of 80% chloroform/20% methanol at ambient temperature (approximately 21-22° C.).

A stainless steel stent 18 mm in length was obtained and prepared by first applying a layer of parylene C using a vapor-deposition technique. After the parylene was disposed onto the stent, the coating solution was applied to the stent using an ultrasonic spray technique. A total coating weight of 683 μg was applied to the stent (measured after the solvent had substantially evaporated off) resulting in a drug loading of approximately 225 μg of estradiol.

Figure 4:
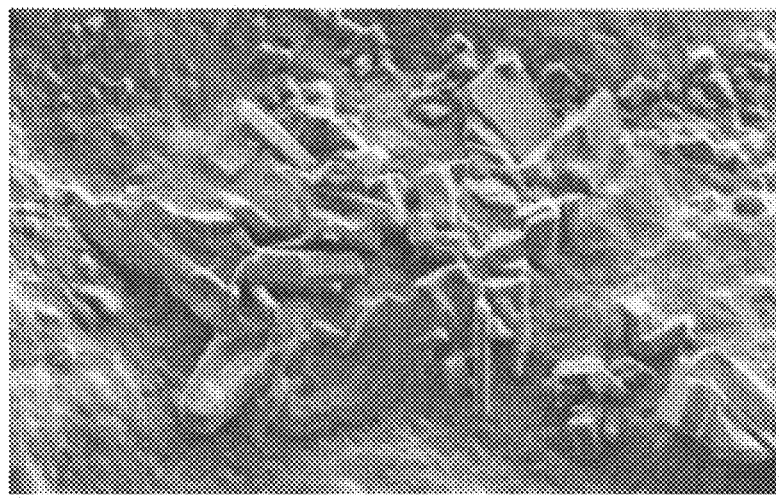
FIG. 4 is an image of the surface features of a coating on a device taken using SEM.

After 8 days, the surface of the stent was examined using scanning electron microscopy (SEM) at various magnifications. A 7500× view is shown in FIG. 4. SEM analysis revealed that there were significant quantities of crystals coming out of the surface of the coating.

Example 4: Saturated Coating Composition with Toluene/THF/Isopropyl Alcohol Solvent Estradiol was combined with THF. Polyethylenevinylacetate (PEVA), and poly-n-butyl methacrylate (PBMA) was combined with a solution containing eight parts toluene and one part isopropyl alcohol. The estradiol solution was combined with the PEVA/PBMA solution to form a coating solution containing equal weight proportions of estradiol, PEVA, and PBMA and a solvent containing 80% toluene, 10% THF, and 10% isopropyl alcohol, with a total solids concentration of 40 mg/ml (33% PEVA/33% PBMA/33% estradiol). The resulting solution was approximately at the saturation point for estradiol in a solvent of 80% toluene, 10% THF, and 10% isopropyl alcohol at ambient temperature (approximately 21-22° C.).

Two stainless steel stents (A and B) 18 mm in length were obtained and prepared by first applying a layer of parylene C using a vapor-deposition technique. After the parylene was disposed onto the stents, the coating solution was applied to the stent using an ultrasonic spray technique at a relative humidity of 10%. A total coating weight of 688 μg was applied to stent A (measured after the solvent had substantially evaporated off) resulting in a drug loading of approximately 227 μg of estradiol. A total coating weight of 659 μg was applied to stent B (measured after the solvent had substantially evaporated off) resulting in a drug loading of approximately 217 μg of estradiol.

Figure 5:
FIG. 5 is an image of a coating on a device taken using darkfield microscopy.

After the coating process was completed, stent B was evaluated for crystal formation using darkfield microscopy. Darkfield microscopy shows the formation of crystals not just at the surface of the coating but throughout the coating thickness. FIG. 5 shows a darkfield image of the coating on stent B. This darkfield image shows active agent crystals over substantially 100% of the coating (within the coating). In contrast to FIG. 1 in example 2 above, this example demonstrates that rapid crystallization occurs when using a saturated coating solution.

Figure 6:
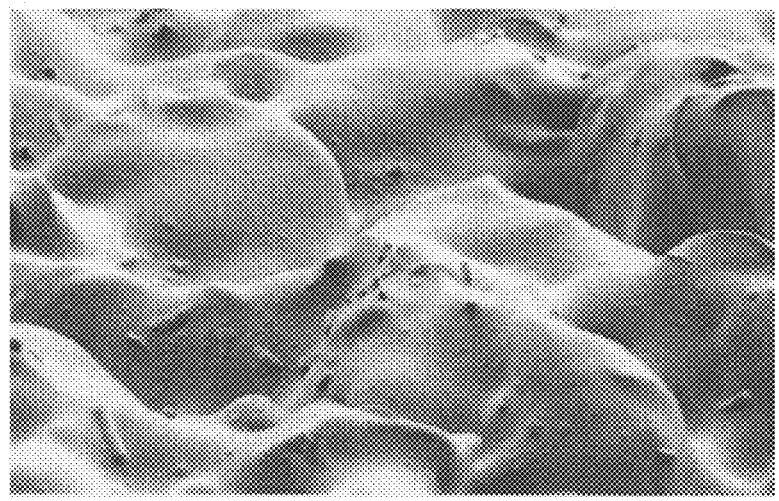
FIG. 6 is an image of the surface features of a coating on a device taken using SEM.

After 7 days, the surface of stent A was examined using scanning electron microscopy (SEM) at various magnifications. A 7500× view is shown in FIG. 6. SEM analysis revealed that there was crystal formation but that these crystals did not come out of, or erupt, through the surface of the coating.

This example shows that applying a coating solution that was saturated with the active agent reduced the amount of crystals that erupted through the surface of the coating.

Example 5: Saturated Coating Composition with Toluene/THF Solvent

Estradiol was combined with THF. Two parts by weight of polyethylenevinylacetate (PEVA) was combined with five parts by weight of poly-n-butyl methacrylate (PBMA) in toluene. The estradiol solution was combined with the PEVA/PBMA solution to form a coating solution containing 40 mg/ml total solids (30 wt. % estradiol, 20 wt. % PEVA, and 50 wt. % PBMA) and a solvent containing 80% toluene and 20% THF. The resulting solution was near the saturation point for estradiol in a solvent of 80% toluene and 20% THF at ambient temperature (approximately 21-22° C.).

A stainless steel stent 28 mm in length was obtained and prepared by first applying a layer of parylene C using a vapor-deposition technique. After the parylene was disposed onto the stent, the coating solution was applied to the stent using an ultrasonic spray technique at a relative humidity of 30%. A total coating weight of 2015 μg was applied to the stent (measured after the solvent had substantially evaporated off) resulting in a drug loading of approximately 605 μg of estradiol.

Figure 7:
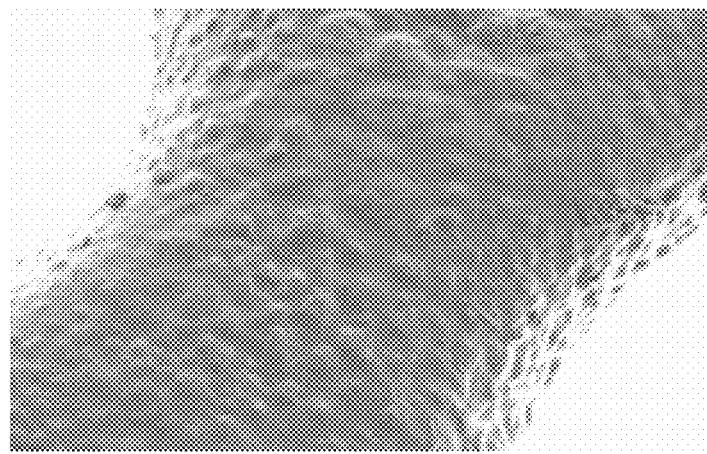
FIG. 7 is an image of the surface features of a coating on a device taken using SEM.

After 7 days, the surface of the stent was examined using scanning electron microscopy (SEM) at various magnifications. FIG. 7 shows the surface of the coating at 500× magnification. SEM analysis revealed that the surface was somewhat bumpy but that there were substantially no crystals coming out of, or erupting through, the surface of the coating.

This example shows that applying a coating solution that is saturated with the active agent (or near saturation) can reduce the amount of crystals that erupt through the surface of the coating.

Example 6: Unsaturated Coating Composition with Toluene/THF Solvent

Estradiol was combined with THF. Two parts by weight of polyethylenevinylacetate (PEVA) was combined with five parts by weight of poly-n-butyl methacrylate (PBMA) in toluene. The estradiol solution was combined with the PEVA/PBMA solution to form a coating solution containing 30 mg/ml total solids (30 wt. % estradiol, 20 wt. % PEVA, and 50 wt. % PBMA) and a solvent containing 80% toluene and 20% THF. The resulting solution had an estradiol concentration that was less than the saturation point for a solvent of 80% toluene and 20% THF at ambient temperature (approximately 21-22° C.). The distinction between this example and example 4 is that here the total solids concentration was only 30 mg/ml instead of 40 mg/ml. Thus the concentration of estradiol was at less than the saturation point.

A stainless steel stent 28 mm in length was obtained and prepared by first applying a layer of parylene C using a vapor-deposition technique. After the parylene was disposed onto the stent, the coating solution was applied to the stent using an ultrasonic spray technique at a relative humidity of 30%. A total coating weight of 1000 µg was applied to the stent (measured after the solvent had substantially evaporated off) resulting in a drug loading of approximately 300 µg of estradiol. The coating was evaluated under a microscope at 50× magnification (not shown). The coating had a patchy appearance and the formation of large crystals was observed. This coating had an appearance similar to that which could be observed with other non-saturated solutions such as in Examples 2 and 3 above.

This example shows that when a coating solution is applied wherein the concentration of the active agent is below the saturation point, the crystallization process may result in the formation of large crystals.

Example 7: Non-Saturated Coating Composition with THF Solvent and Topcoat

Estradiol, polyethylenevinylacetate (PEVA), and poly-n-butyl methacrylate (PBMA) were combined in THF to result in weight proportions of 30% estradiol, 20% PEVA, and 50% PBMA for a total solids concentration of 40 mg/ml. The resulting solution had a estradiol concentration that was less than the saturation point for a solvent of 100% THF at ambient temperature (approximately 21-22° C.).

A stainless steel stent 9 mm in length was obtained and prepared by first applying a layer of parylene C using a vapor-deposition technique. After the parylene was disposed onto the stent, the coating solution was applied to the stent using an ultrasonic spray technique at a relative humidity of 30%. A total coating weight of 615 µg was applied to the stent (measured after the solvent had substantially evaporated off) resulting in a drug loading of approximately 185 µg of estradiol.

Next, a topcoat solution was formed by mixing PBMA with THF to form a solution with a total solids concentration of 10 mg/ml. The topcoat solution was applied to the stent using an ultrasonic spray technique at a relative humidity of 30%, resulting in a topcoat weight of 107 µg (measured after the solvent had substantially evaporated off).

Figure 8:
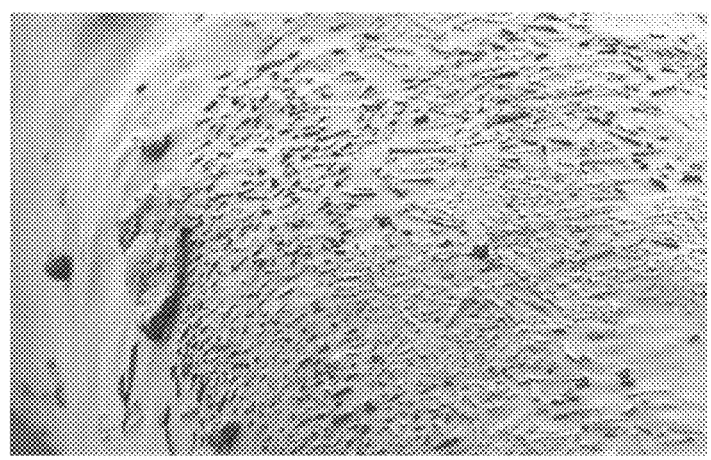
FIG. 8 is an image of the surface features of a coating on a device taken using SEM.

After 7 days, the surface of the stent was examined using scanning electron microscopy (SEM) at various magnifications. FIG. 8 shows a view of the topcoat surface at 1000× magnification. SEM analysis revealed that there were significant amounts of crystals coming out of, or erupting through, the surface of the topcoat.

This example shows that when a coating solution is applied wherein the concentration of the active agent is below the saturation point, even where a topcoat is added, the crystallization process can result in crystals of the active agent erupting through the coating surface.

Example 8: Saturated Coating Composition with Toluene/THF Solvent and Topcoat Estradiol was combined with THF. Two parts by weight of polyethylenevinylacetate (PEVA) was combined with five parts by weight of poly-n-butyl methacrylate (PBMA) in toluene. The estradiol solution was combined with the PEVA/PBMA solution to form a coating solution containing 40 mg/ml total solids (30 wt. % estradiol, 20 wt. % PEVA, and 50 wt. % PBMA) and a solvent containing 80% toluene and 20% THF. The resulting solution was approximately at the saturation point for estradiol in a solvent of 80% toluene and 20% THF at ambient temperature (approximately 21-22° C.).

A stainless steel stent 28 mm in length was obtained and prepared by first applying a layer of parylene C using a vapor-deposition technique. After the parylene was disposed onto the stent, the coating solution was applied to the stent using an ultrasonic spray technique at a relative humidity of 30%. A total coating weight of 2094 µg was applied to the stent (measured after the solvent had substantially evaporated off) resulting in a drug loading of approximately 629 µg of estradiol.

Next, a topcoat solution was formed by mixing PBMA with toluene to form a solution with a total solids concentration of 30 mg/ml. The topcoat solution was applied to the stent using an ultrasonic spray technique at a relative humidity of 10%, resulting in a topcoat weight of 297 µg (measured after the solvent had substantially evaporated off).

Figure 9:
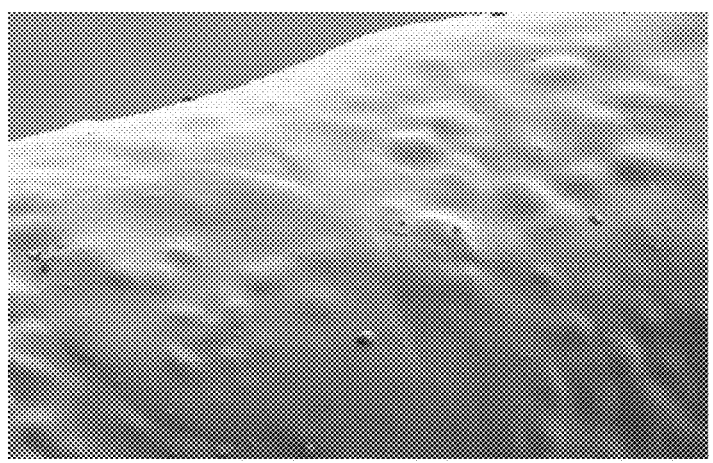
FIG. 9 is an image of the surface features of a coating on a device taken using SEM.

After 7 days, the surface of the stent was examined using scanning electron microscopy (SEM) at various magnifications. FIG. 9 shows the surface of the topcoat at 1000× magnification. SEM analysis revealed that there were substantially no crystals coming out of, or erupting through, the surface of the coating.

This example shows that applying a coating solution that is saturated with the active agent can reduce the amount of crystals that erupt through the surface of the coating.

Example 9: Saturated Versus Unsaturated Coating Compositions Including Dexamethasone To form a saturated coating solution (solution one), dexamethasone (DEX) was combined with polybutadiene (PBD) (MW 160 kD) and poly(n-butyl methacrylate) (pBMA) (MW 250 kD) in a solvent mixture of 58% THF and 42% chloroform. The saturated coating solution was made by adding 75 mg of pBMA and 75 mg of PBD to 5 ml of chloroform on a stir-plate. To this solution, 150 mg of DEX was added. THF was slowly added to the stirring mixture until the resulting solution turned clear. A total of 7 ml of THF was added. The resulting coating solution had a total solids content of 25 mg/ml including (50% DEX), (25% PBD), and (25% pBMA).

To form an unsaturated control coating solution (solution two), DEX was combined with polybutadiene (PBD) (MW 160 kD) and poly(n-butyl methacrylate) (pBMA) (MW 250 kD) in a solvent of 100% tetrahydrofuran (THF). The resulting coating solution had a total solids content of 25 mg/ml including (50% DEX), (25% PBD), and (25% pBMA).

Four stainless steel stents (OrbusNeich, Netherlands) 18 mm in length were obtained. Coating solution one was applied to two stents (1 and 2) using an ultrasonic spray technique at a relative humidity of 30%. Similarly, coating solution two was applied to two stents (3 and 4) using an ultrasonic spray technique at a relative humidity of 30%.

Figure 10:
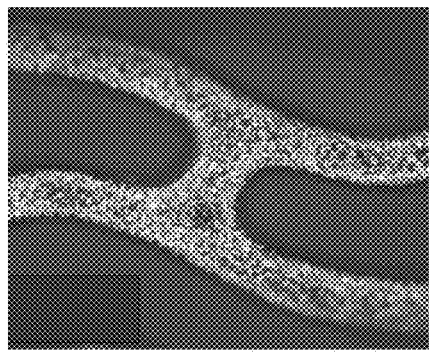
FIG. 10 is a series of six images of two different coatings taken over a period of two weeks using polarized light optical microscopy.
Figure 10:
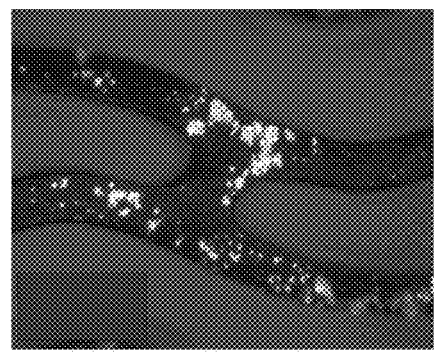
Figure 10:
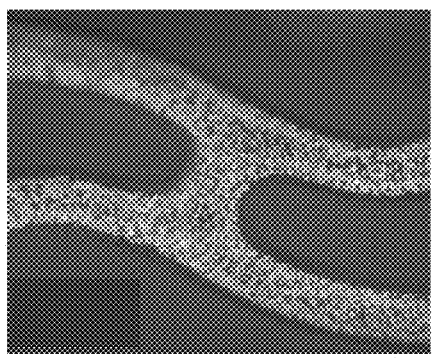
Figure 10:
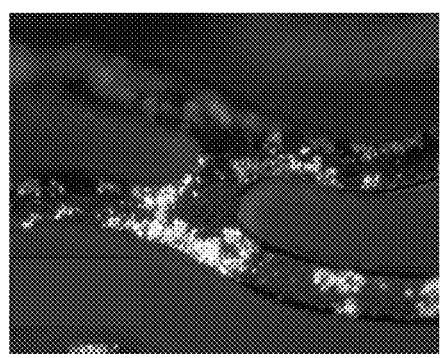
Figure 10:
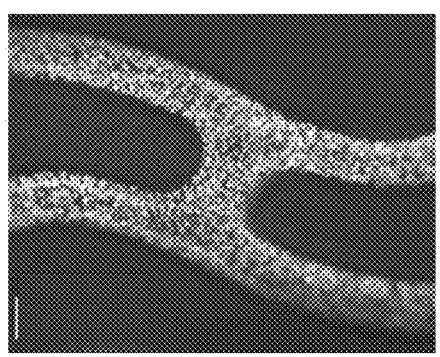
Figure 10:
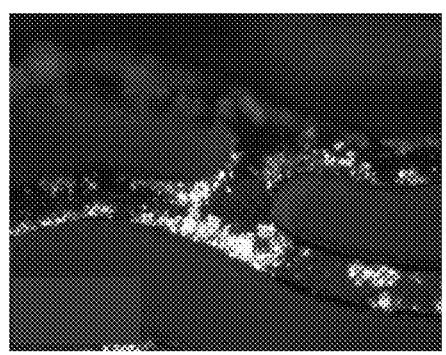

The surface of the stents was examined using polarized light optical microscopy at days 0, 7, and 14. Polarized light microscopy shows the amount of crystallization throughout the entire coating thickness. FIG. 10, panels A, B, and C, show a representative portion of stent 1 (saturated) at 100× magnification. FIG. 10, panel A, shows that on day 0, stent 1 was approximately 100% crystallized. FIG. 10, panels B and C show that stent 1 remained approximately 100% crystallized on days 7 and 14 respectively. FIG. 10, panels D, E, and F, show a representative portion of stent 3 (unsaturated) at 100× magnification. FIG. 10, panel D, shows that on day 0, stent 3 was roughly 10% crystallized. FIG. 10, panels E and F, show that the degree of crystallization on stent 3 increased over a period of two weeks but remained less than 50% crystallized. A similar pattern was demonstrated when comparing the crystallization trends of stents 2 (saturated) and 4 (unsaturated).

Figure 11:
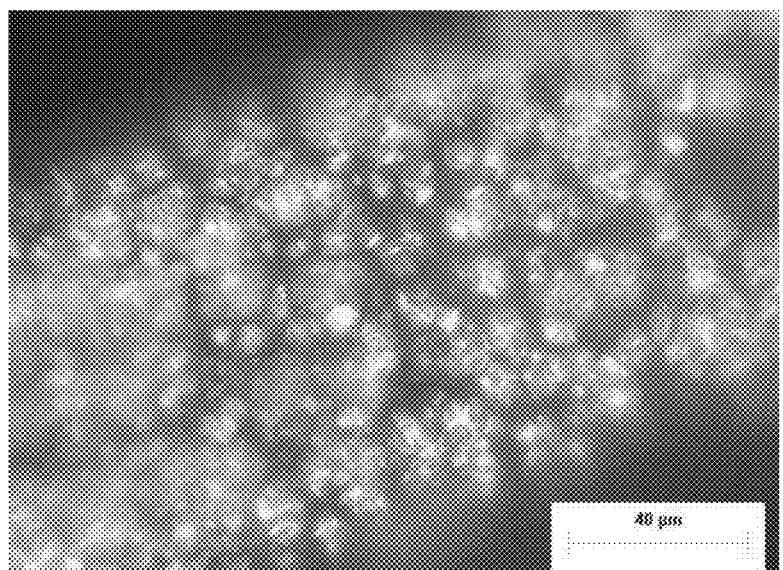
FIG. 11 is a series of two images of two different coatings taken using polarized light optical microscopy at high magnification showing the distinction in crystal sizes between the two different coatings.
Figure 11:
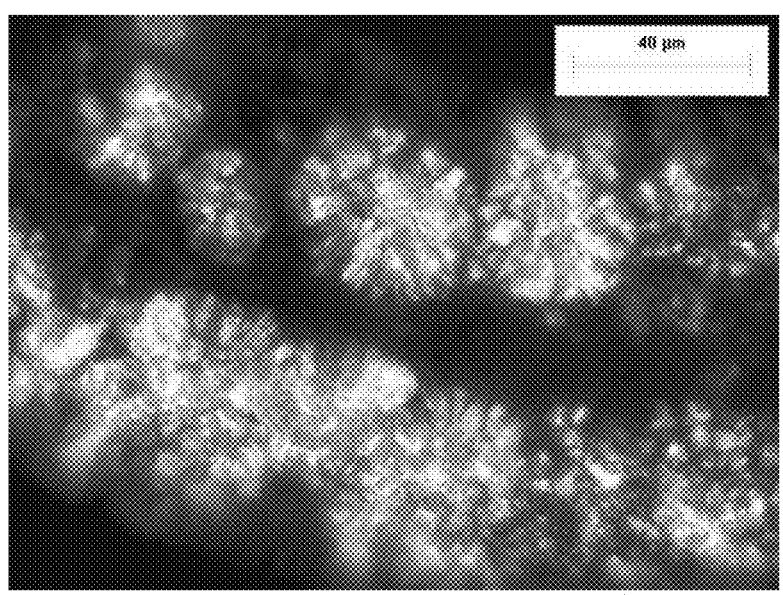

Portions stents 2 and 4 that had crystals were then evaluated using polarized light optical microscopy at a higher magnification (500×) to further characterize the differences between the two. The results are shown in FIG. 11, panels A and B. The crystals in panel A (formed from a saturated coating solution) are clearly smaller than those shown in panel B (formed from an unsaturated coating solution).

This example shows that saturated coating solutions can be used to enhance the formation of active agent crystals in the resulting coating. Specifically, this example shows that saturated coating solutions can be used to accelerate the crystallization process in elution control coatings. This example also shows that the use of saturated coating solutions results in smaller more uniform crystals than does the use of unsaturated coating solutions.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration to. The phrase "configured" can be used interchangeably with other similar phrases such as arranged and configured, constructed and arranged, constructed, manufactured and arranged, and the like.

All publications and patent applications in this specification are indicative of the level of ordinary skill in the art to which this invention pertains. All publications and patent applications are herein incorporated by reference to the same extent as if each individual publication or patent application was specifically and individually indicated by reference.

The invention has been described with reference to various specific and preferred embodiments and techniques. However, it should be understood that many variations and modifications may be made while remaining within the spirit and scope of the invention.

The invention claimed is:

1. A method for applying an active agent in a coating onto a medical device, the method comprising:
    selecting a solvent and a hydrophobic polymer, wherein the polymer and solvent form a true solution;
    selecting a concentration of an active agent, wherein the concentration of active agent is at least 80% of saturation in a composition comprising the solvent and about 1.0 to about 99.0 wt. % polymer;
    combining the active agent, the polymer, and the solvent to form a coating composition having the selected concentration of the active agent;
    applying the coating composition to the medical device; and evaporating the solvent leaving behind crystals of the active agent;
    the active agent selected from the group consisting of paclitaxel, rapamycin and rapalogs.

2. The method of claim 1, the active agent comprising paclitaxel.

3. The method of claim 1, the active agent comprising rapamycin.

4. The method of claim 1, the hydrophobic polymer have a solubility parameter of less than about 10.0 $(cal/cm^3)^{1/2}$.

5. The method of claim 1, the hydrophobic polymer comprises a first polymer component comprising at least one poly(alkyl)(meth)acrylate and a second polymer component comprising poly(ethylene-co-vinyl acetate), wherein the second polymer component is selected from the group consisting of poly(ethylene-co-vinyl acetate) polymers having vinyl acetate concentrations of between about 10% and about 50% by weight.

6. The method of claim 1, wherein the active agent is at least 95% crystallized.

* * * * *